US012673078B2

(12) United States Patent
Kilcher et al.

(10) Patent No.: US 12,673,078 B2
(45) Date of Patent: Jul. 7, 2026

(54) BACTERIOPHAGES PRODUCING HETEROLOGOUS BACTERIOCINS

(71) Applicant: ETH Zurich, Zürich (CH)

(72) Inventors: Samuel Nando Kilcher, Zürich (CH); Matthew Stephen Dunne, Zürich (CH); Susanne Andrea Meile, Zürich (CH); Jiemin Du, Zürich (CH); Martin Johannes Loessner, Zürich (CH)

(73) Assignee: ETH Zurich, Zürich (CH)

( * ) Notice: Subject to any disclaimer, the term of this patent is extended or adjusted under 35 U.S.C. 154(b) by 0 days.

(21) Appl. No.: 18/344,998

(22) Filed: Jun. 30, 2023

(65) Prior Publication Data

US 2024/0148806 A1 May 9, 2024

Related U.S. Application Data

(62) Division of application No. PCT/EP2022/077385, filed on Sep. 30, 2022.

(30) Foreign Application Priority Data

Oct. 1, 2021 (EP) ..................................... 21200534

(51) Int. Cl.
| | |
|---|---|
| *A61K 35/76* | (2015.01) |
| *A61P 31/04* | (2006.01) |
| *C07K 14/195* | (2006.01) |
| *C12N 7/00* | (2006.01) |

(52) U.S. Cl.
CPC .............. *A61K 35/76* (2013.01); *A61P 31/04* (2018.01); *C07K 14/195* (2013.01); *C12N 7/00* (2013.01); *C12N 2795/00022* (2013.01); *C12N 2795/00032* (2013.01)

(58) Field of Classification Search
None
See application file for complete search history.

(56) References Cited

U.S. PATENT DOCUMENTS

| | | |
|---|---|---|
| 2014/0148379 A1 | 5/2014 | Liu et al. |
| 2015/0320829 A1 | 11/2015 | Liu et al. |

FOREIGN PATENT DOCUMENTS

EP 3584316 A1 12/2019

OTHER PUBLICATIONS

Witkowski et al, Biochemistry 38:11643-11650, 1999. (Year: 1999).*
Seffernick et al, Bacteriol. 183(8): 2405-2410, 2001. (Year: 2001).*
Prengler et al, Ann Neurol 2002; 51:543-552. (Year: 2002).*
Masuda, Y., Kawabata, S., Uedoi, T., Honjoh, K.I. and Miyamoto, T., 2021. Construction of leaderless-bacteriocin-producing bacteriophage targeting *E. coli* and neighboring gram-positive pathogens. Microbiology spectrum, 9(1), pp. e00141-e00121.
Hupfeld, M., Trasanidou, D., Ramazzini, L., Klumpp, J., Loessner, M.J. and Kilcher, S., 2018. A functional type II-A CRISPR-Cas system from Listeria enables efficient genome editing of large non-integrating bacteriophage. Nucleic acids research, 46(13), pp. 6920-6933.
Cherier, D., Patin, D., Blanot, D., Touzé, T. and Barreteau, H., 2021. The Biology of Colicin M and Its Orthologs. Antibiotics, 10(9), p. 1109.
Flores-Mireles, A.L., Walker, J.N., Caparon, M. and Hultgren, S.J., 2015. Urinary tract infections: epidemiology, mechanisms of infection and treatment options. Nature reviews microbiology, 13(5), pp. 269-284.

* cited by examiner

*Primary Examiner* — Daniel E Kolker
*Assistant Examiner* — Cheom-Gil Cheong
(74) *Attorney, Agent, or Firm* — Ipsilon USA—NLO

(57) ABSTRACT

The present invention relates to the field of medicine, specifically the field of bacterial infection and treatment thereof.

13 Claims, 23 Drawing Sheets

Specification includes a Sequence Listing.

Bacteriophage::bacteriocin

✧ Bacteriocin

Fig. 2B

| Strain | Species | Efs3::kvarM | Efs7::kvarM |
|---|---|---|---|
| A Kp3 | K. pneumoniae | ++ | ++ |
| B Kp37 | K. pneumoniae | +++ | +++ |
| C Kp31 | K. pneumoniae | + | + |
| D Kp39 | K. pneumoniae | - | - |
| E Kp5 | K. pneumoniae | - | - |
| F Kp33 | K. pneumoniae | +++ | +++ |
| G Kp21 | K. pneumoniae | - | - |
| H Kp43 | K. pneumoniae | + | - |
| J Kp16 | K. pneumoniae | (+) | - |
| K Kp34 | K. pneumoniae | - | - |
| L Kp48 | K. pneumoniae | - | - |
| M Kp45 | K. pneumoniae | ++ | ++ |
| N Kp26 | K. pneumoniae | + | + |
| O Kp8 | K. pneumoniae | - | - |
| P KpGe | K. pneumoniae | ++ | ++ |
| Q Kp22 | K. pneumoniae | (±) | (±) |
| R Kp51 | K. pneumoniae | +++ | +++ |
| S Kp36 | K. pneumoniae | ++ | ++ |
| T Kp6 | K. pneumoniae | ++ | ++ |
| U Kp53 | K. pneumoniae | - | - |
| V Kp66 | K. pneumoniae | + | - |
| Y Kp69 | K. pneumoniae | + | - |

| Strain | Species | K1::colM | K1::colE6 | CM001::colE7 | Efs3::colE7 | Efs3::colM | Efs7::colM |
|---|---|---|---|---|---|---|---|
| A Ec3 | E.coli | - | - | + | - | - | - |
| B Ec22 | E.coli | - | - | - | - | - | - |
| C Ec42 | E.coli | - | - | - | - | - | - |
| D Ec43 | E.coli | - | ++ | +++ | +++ | - | - |
| E Ec16 | E.coli | - | + | +++ | +++ | - | - |
| F Ec32 | E.coli | +++ | - | - | - | - | - |
| G Ec46 | E.coli | - | - | +++ | + | ++ | ++ |
| H Ec57 | E.coli | - | - | - | - | - | - |
| J Ec14 | E.coli | - | - | - | - | ++ | - |
| K Ec33 | E.coli | - | - | - | - | - | - |
| L Ec47 | E.coli | - | + | +++ | ++ | + | + |
| M Ec54 | E.coli | - | + | +++ | +++ | - | - |
| N Ec20 | E.coli | ++ | + | +++(host) | +++ | +++ | + |
| O Ec34 | E.coli | - | - | - | - | - | - |
| Q Ec41 | E.coli | - | ++ | +++ | +++ | - | - |
| R Ec62 | E.coli | - | - | - | - | - | - |
| S Ec21 | E.coli | + | - | ++ | ++ | + | - |
| T Ec28 | E.coli | - | ++ | ++ | ++ | + | - |
| V Ec52 | E.coli | - | - | ++ | +++ | - | - |
| W Ec63 | E.coli | - | - | - | - | - | - |
| X Ec65 | E.coli | + | - | +++ | +++ | - | - |
| Y Ec56 | E.coli | - | + | +++ | +++ | - | - |
| Z Ec79 | E.coli | - | - | - | - | - | - |
| P (BI21) | E.coli | - | - | + | - | - | - |

CAUTIphage::bacteriocin

Bacteriocin

Starting conditions: $1\times10^8$ CFU/ml + $1\times10^8$ PFU/ml

Starting conditions: $1\times10^8$ CFU/ml + $1\times10^8$ PFU/ml

Co-infection: Ratio 1:1

Co-infection: Ratio 1:10

1. HEPT treatment

2. CLB + phage production

3. Phage-mediated killing and CLB release

4. CLB-mediated killing susceptible resistant

HEPT bacteriocin

E2 hoc hoc 1 kb

K1 gp168 gp168

☐ = WT phage

▨ = colE7

▦ = kvarM

▽ = effector gene insertion site

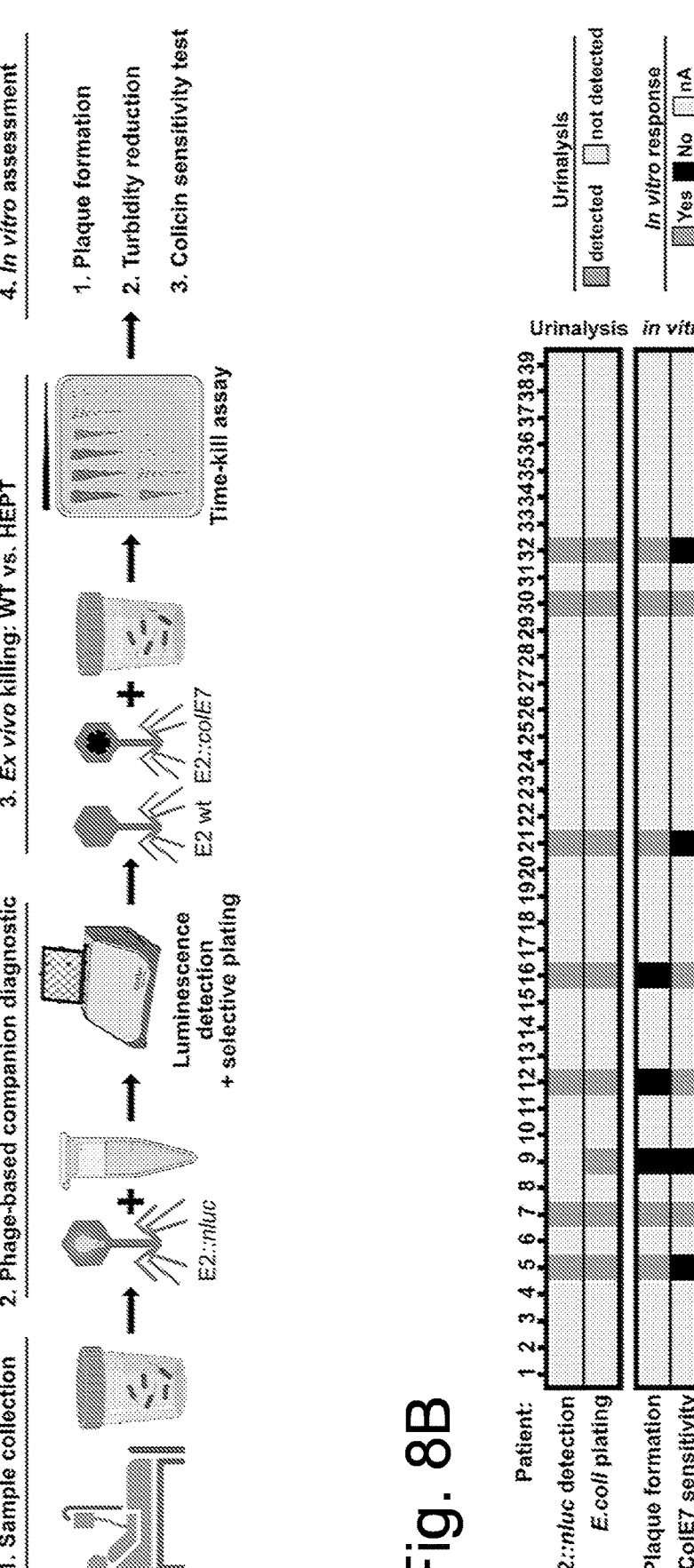

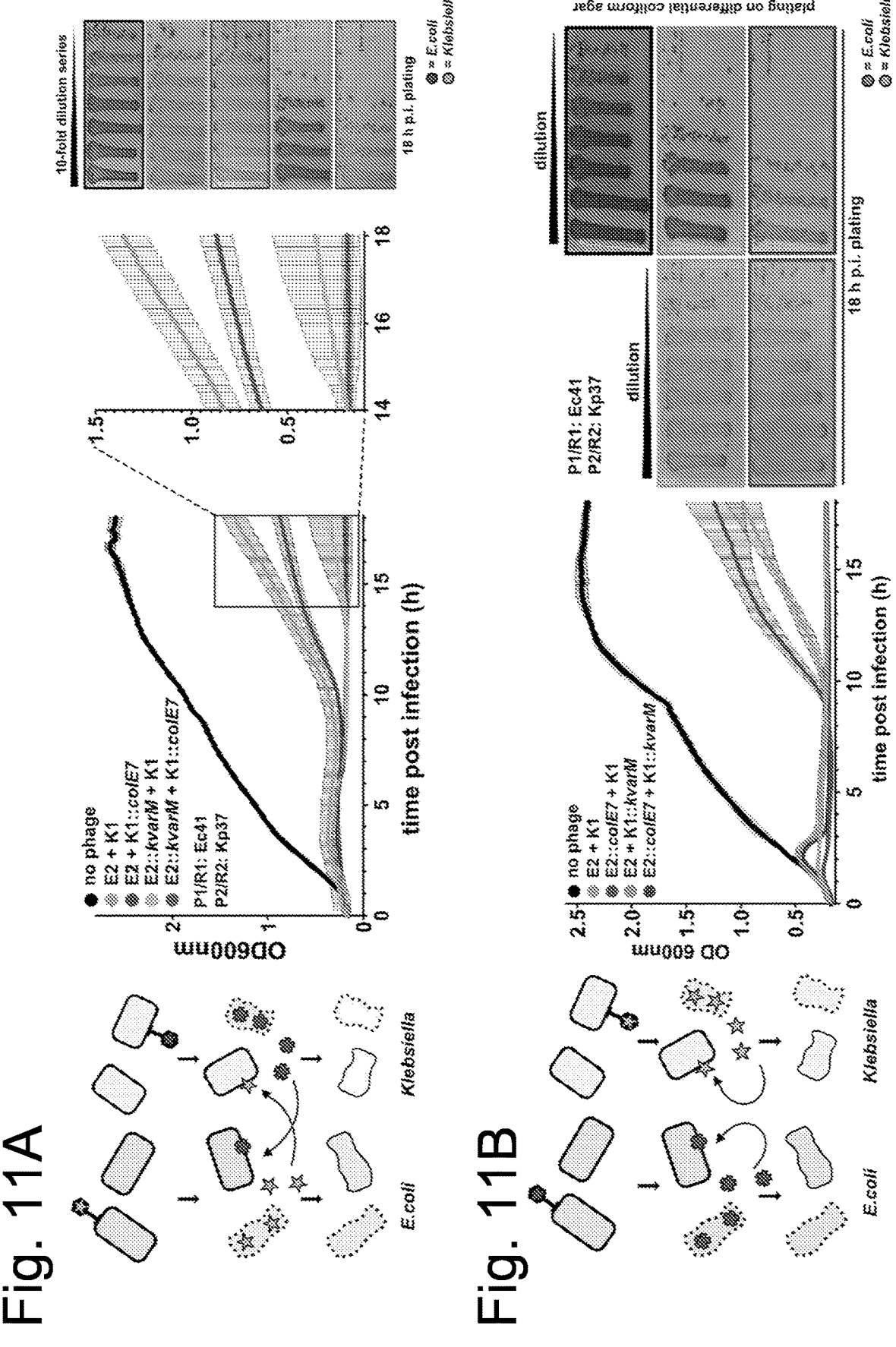

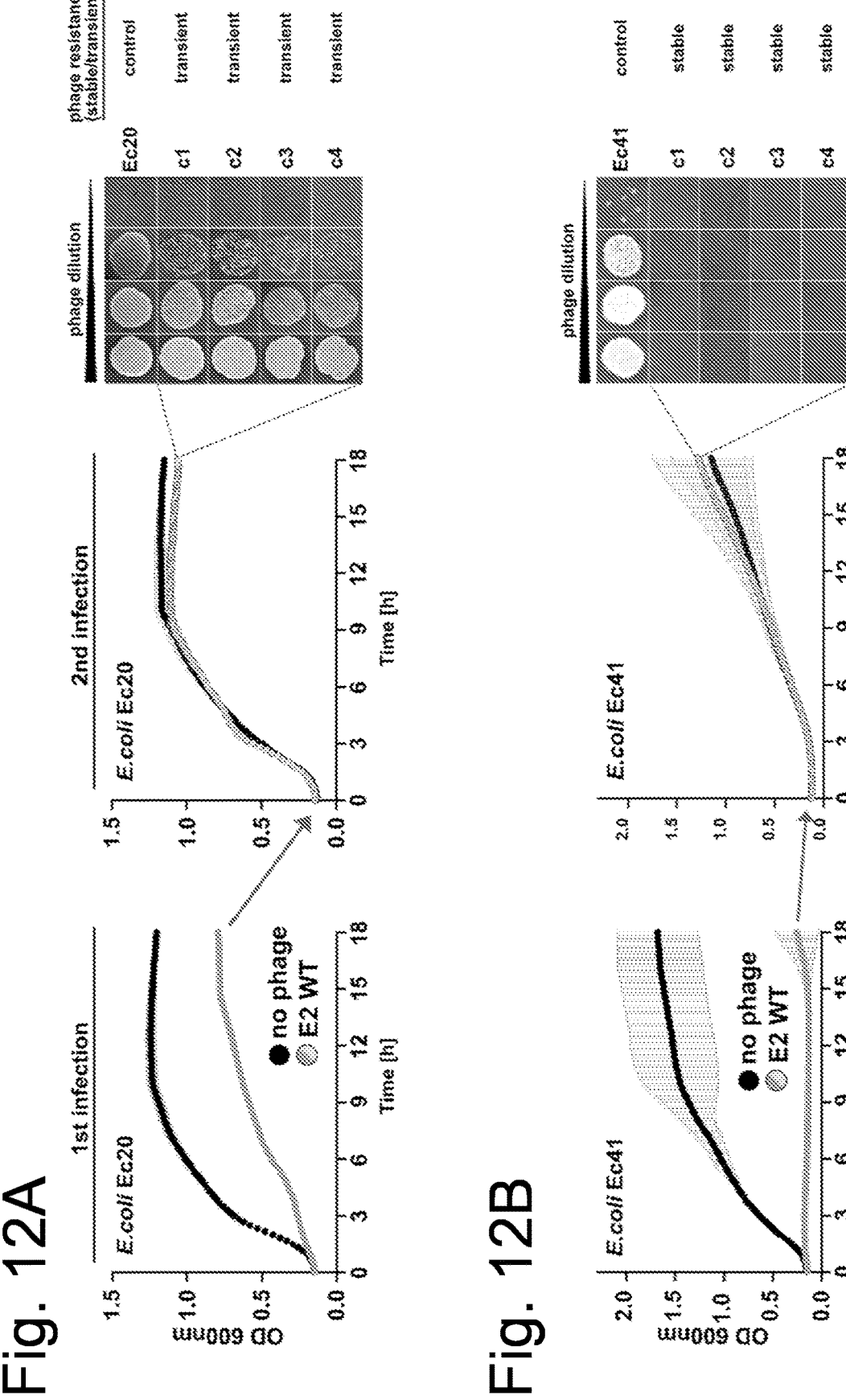

Fig. 14C
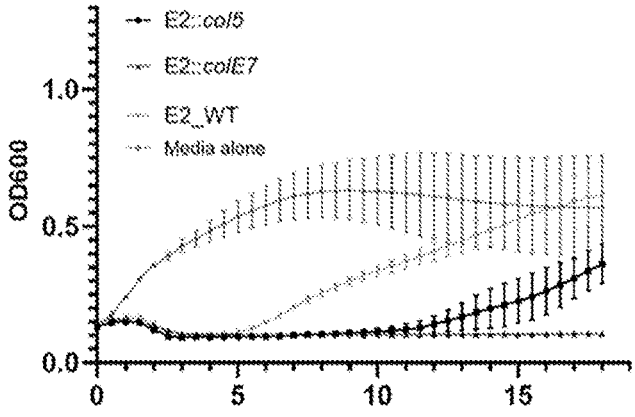
Fig. 14D
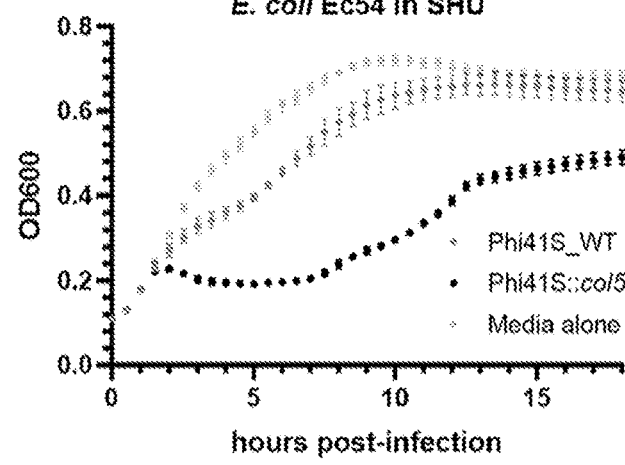
Fig. 14E

BACTERIOPHAGES PRODUCING HETEROLOGOUS BACTERIOCINS

REFERENCE TO AN ELECTRONIC SEQUENCE LISTING

The contents of the electronic sequence listing (P6106044US1 wiposequence St26.xml.; Size: 3.31 MB; and Date of Creation: Jun. 21, 2023) is herein incorporated by reference in its entirety.

FIELD OF THE INVENTION

The present invention relates to the field of medicine, specifically the field of bacterial infection and treatment thereof.

BACKGROUND OF THE INVENTION

The antibiotic resistance crisis and adverse effects caused by antibiotic-induced microbiome dysbiosis highlight the need for novel and more pathogen-specific antibacterial interventions. The therapeutic use of bacteriophages/phages (i.e., viruses that infect bacteria) is one promising alternative option. While phages offer the required pathogen-specificity, it remains difficult to completely inactivate all cells from a population of target cells. This is due to the evolution of effective phage resistance mechanisms such as receptor diversification, adaptive CRISPR-Cas immunity, restriction/modification, or abortive infection that bacteria use to counteract phage predation. To circumvent this limitation, multiple phages with distinct infection pathways are typically combined to replace or complement antibiotic therapy with varying results.

Accordingly, there is a need to further improve pathogen-specific antibacterial interventions.

DESCRIPTION OF THE INVENTION

The inventors have established that bacteriophages can be engineered to encode bacteriocins as genetic payloads. Heterologous bacteriocins can be expressed during infection and can be released upon host cell lysis to locally improve and expand the antibacterial effect of the parental host phage. Bacteriocins may act on species of the host strain itself to target resistant sub-populations and other survivors of phage infection. Alternatively, a bacteriocin may be produced that is not toxic to the host strain but is toxic to another strain, so a second pathogen can be targeted.

Accordingly, in a first aspect there is provided, a modified bacteriophage capable of infecting a host bacterium, wherein the bacteriophage comprises a gene that is foreign to the bacteriophage and wherein said gene encodes a bacteriocin.

In the embodiments herein, 'modified bacteriophage' means that the bacteriophage is genetically modified such that the genome comprises a gene that is foreign to the bacteriophage and which gene encodes a bacteriocin which is antibacterial enzyme that targets species of the host bacterium. The person skilled in the art knows how to modify a genome of a bacteriophage. To be able to express the bacteriocin, the coding sequence may be operable linked to control sequences such as but not limited to a promoter and a terminator sequence. The promoter may be any promotor that is compatible with the target bacterium and may be a constitutive or an inducible promotor. The coding sequence of the bacteriocin may be codon optimized for optimal expression in the target bacterium. The modified bacteriophage may further comprise a selectable marker, which may be a dominant or an auxotrophic marker. The marker may be an antibiotic or a non-antibiotic marker. The marker may be a marker that after engineering the genome can be deleted. The genome of the bacteriophage may be modified by a polynucleotide-guided genome editing system such as a CRISPR-Cas system or variant thereof.

Bacteriocins are known to the person skilled in the art and are toxins that inhibit the growth of bacteria. Since they can be specific for species of bacteria, the can be used to selectively target bacteria within a microbiome without targeting other bacteria in the microbiome, unlike antibiotics which typically target large groups of bacteria.

In the embodiments herein, the bacteriocin may be any bacteriocin that can be encoded by a gene within a modified bacteriophage. The bacteriocin may be a peptide or a polypeptide, the polypeptide may be an enzyme such as the chimeric endolysin EC300 as described in the examples herein or a functional variant of EC300 having at least 50% sequence identity to SEQ ID NO: 32. Another example of a bacteriocin enzyme is the nuclease Colicin E7 as described elsewhere herein. In an embodiment, the bacteriocin is not lysostaphin. In an embodiment, the bacteriocin is not ALE-1. In an embodiment, the bacteriocin is not Lacticin Q.

In the embodiments herein, the bacteriocin may a bacteriocin specific for Gram-negative bacteria, such as a microcin, a colicin-like bacteriocin or a tailocin.

In the embodiments herein, the bacteriocin is a bacteriocin specific for Gram-positive bacteria, such as class III bacteriocins.

In the embodiments herein, the bacteriocin may target species of the host bacterium. This means that a population of host bacteria is not only targeted and inhibited in growth by the bacteriophage, but also by the bacteriocin. In case where a bacterium within the population would be resistant or tolerant to the bacteriophage, it may still be killed by the bacteriocin.

In the embodiments herein, the bacteriocin may not target species of the host bacterium. This means that the host bacterium is targeted by the bacteriophage and may be inhibited in growth by the bacteriophage, but the host bacterium is not targeted and not inhibited in growth by the bacteriocin. The bacteriocin may target other bacterial species present in the microbiome or infection and may inhibit growth of these species.

In the embodiments herein, the bacteriocin may have a protein sequence that can be classified into an InterPro homologous superfamily, family, or domain selected from the group consisting of: IPR036725, IPR037146, IPR038283, IPR036302, IPR024575, IPR028056, IPR000293, IPR009105, IPR024566, and IPR016128. The bacteriocin protein sequence may be classified as homologous superfamily IPR036725, IPR037146, IPR038283, or IPR036302; may be classified as family IPR024575 or IPR028056, or may be classified as domain IPR000293, IPR009105, IPR024566, or IPR016128. InterPro classification of protein families is known to the person skilled in the art and provides functional analysis of proteins by classifying them into families and predicting domains and important sites. To classify proteins in this way, InterPro uses predictive models, known as signatures, provided by several different databases (referred to as member databases) that make up the InterPro consortium. InterPro combines protein signatures from these member databases into a single searchable resource, capitalising on their individual strengths to produce a powerful integrated database and diagnostic tool. See e.g. www.ebi.ac.uk/interpro and Blum et al, 2020 (The InterPro protein families and domains database: 20 years on. *Nucleic Acids Research*, November 2020, (doi: 10.1093/nar/gkaa977).

In the embodiments herein, the bacteriocin may be selected from the group consisting of Colicin M, Colicin E7, Colicin K, Colicin 5, Colicin E6 and Klebicin M.

In the embodiments herein, the bacteriocin may have at preferably at least 50% sequence identity with a bacteriocin selected from the group consisting of Colicin M (SEQ ID NO: 18), Colicin E7 (SEQ ID NO: 20), Colicin K (SEQ ID NO: 19), Colicin 5 (SEQ ID NO: 17), Colicin E6 (SEQ ID NO: 16) and Klebicin M (SEQ ID NO: 21) while preferably maintaining its wild-type bacteriocin functionality. Such bacteriocin may also be a variant bacteriocin that has different properties compared to the corresponding wild-type bacteriocin and may e.g. have altered host specificity or altered specific activity.

In the embodiments herein, the host bacterium may be any bacterium known to the person skilled in the art. In the embodiments herein, the host bacterium may a bacterium selected from the group consisting of: *Acetinobacter, Chroinobacter, Bortadella, Burkholderia, Campylobacter, Staphylococcus, Pneumococcus, Enterococcus*, such as *Enterococcus faecalis, Klebsiella*, such as *Klebsiella pneumoniae, Escherichia*, such as *E. coli, Pseudomonas, Salmonella, Shigella, Vibrio, Neisseria, Brucella, Haemophilus, Mycobacterium, Listeria, Legionella, Yersinia, Chlamydia, Clostridium, Helicobacter, Corynebacterium, Lactobacillus, Lactococcus, Fusobacterium*, and *Streptococcus.*

In an embodiment, the host bacterium is an *E. coli* species and the bacteriocin targets said *E. coli* species.

In an embodiment, the host bacterium is an *E. coli* species and the bacteriocin does not target said *E. coli* species.

In an embodiment, the host bacterium is an *Enterococcus* species, such as *Enterococcus faecalis*, and the bacteriocin targets said *Enterococcus* species.

In an embodiment, the host bacterium is an *Enterococcus* species, such as *Enterococcus faecalis*, and the bacteriocin does not target said *Enterococcus* species.

In an embodiment, the host bacterium is a *Klebsiella* species, such as *Klebsiella pneumoniae*, and the bacteriocin targets said *Klebsiella* species.

In an embodiment, the host bacterium is a *Klebsiella* species, such as *Klebsiella pneumoniae*, and the bacteriocin does not target said *Klebsiella* species.

In the embodiments herein, the bacteriophage is derived from wild-type bacteriophage *Klebsiella* phage K1*, E. coli* phage CM001, *E. coli* phage E2, *Enterococcus* phage Efs3, *Enterococcus* phage Efs7 or from *E. coli* phage phi41S.

In an embodiment, the bacteriophage is derived from wild-type bacteriophage *Klebsiella* phage K1 and the bacteriocin is Colicin M, or a variant having at least 50% sequence identity to Colicin M (SEQ ID NO: 18).

In an embodiment, the bacteriophage is derived from wild-type bacteriophage *Klebsiella* phage K1 and the bacteriocin is Colicin E7, or a variant having at least 50% sequence identity to Colicin E7 (SEQ ID NO: 20).

In an embodiment, the bacteriophage is derived from wild-type bacteriophage *Klebsiella* phage K1 and the bacteriocin is Colicin E6, or a variant having at least 50% sequence identity to Colicin E6 (SEQ ID NO: 16).

In an embodiment, the bacteriophage is derived from wild-type bacteriophage *Klebsiella* phage K1 and the bacteriocin is Colicin K, or a variant having at least 50% sequence identity to Colicin K (SEQ ID NO: 19).

In an embodiment, the bacteriophage is derived from wild-type bacteriophage *Klebsiella* phage K1 and the bacteriocin is Colicin 5, or a variant having at least 50% sequence identity to Colicin 5 (SEQ ID NO: 17).

In an embodiment, the bacteriophage is derived from wild-type bacteriophage *Klebsiella* phage K1 and the bacteriocin is Klebicin M (kvarM), or a variant having at least 50% sequence identity to Klebicin M (SEQ ID NO: 21).

In an embodiment, the bacteriophage is derived from wild-type bacteriophage *E. coli* phage CM001 and the bacteriocin is Colicin M, or a variant having at least 50% sequence identity to Colicin M (SEQ ID NO: 18).

In an embodiment, the bacteriophage is derived from wild-type bacteriophage *E. coli* phage CM001 and the bacteriocin is Colicin E7, or a variant having at least 50% sequence identity to Colicin E7 (SEQ ID NO: 20).

In an embodiment, the bacteriophage is derived from wild-type bacteriophage *E. coli* phage CM001 and the bacteriocin is Colicin E6, or a variant having at least 50% sequence identity to Colicin E6 (SEQ ID NO: 16), or a variant having at least 50% sequence identity to Colicin E6 (SEQ ID NO: 16).

In an embodiment, the bacteriophage is derived from wild-type bacteriophage *E. coli* phage CM001 and the bacteriocin is Colicin K, or a variant having at least 50% sequence identity to Colicin K (SEQ ID NO: 19).

In an embodiment, the bacteriophage is derived from wild-type bacteriophage *E. coli* phage CM001 and the bacteriocin is Colicin 5, or a variant having at least 50% sequence identity to Colicin 5 (SEQ ID NO: 17).

In an embodiment, the bacteriophage is derived from wild-type bacteriophage *E. coli* phage CM001 and the bacteriocin is Klebicin M (kvarM), or a variant having at least 50% sequence identity to Klebicin M (SEQ ID NO: 21).

In an embodiment, the bacteriophage is derived from wild-type bacteriophage *E. coli* phage E2 and the bacteriocin is Colicin M, or a variant having at least 50% sequence identity to Colicin M (SEQ ID NO: 18).

In an embodiment, the bacteriophage is derived from wild-type bacteriophage *E. coli* phage E2 and the bacteriocin is Colicin E7, or a variant having at least 50% sequence identity to Colicin E7 (SEQ ID NO: 20).

In an embodiment, the bacteriophage is derived from wild-type bacteriophage *E. coli* phage E2 and the bacteriocin is Colicin E6, or a variant having at least 50% sequence identity to Colicin E6 (SEQ ID NO: 16).

In an embodiment, the bacteriophage is derived from wild-type bacteriophage *E. coli* phage E2 and the bacteriocin is Colicin K, or a variant having at least 50% sequence identity to Colicin K (SEQ ID NO: 19).

In an embodiment, the bacteriophage is derived from wild-type bacteriophage *E. coli* phage E2 and the bacteriocin is Colicin 5, or a variant having at least 50% sequence identity to Colicin 5 (SEQ ID NO: 17).

In an embodiment, the bacteriophage is derived from wild-type bacteriophage *E. coli* phage E2 and the bacteriocin is Klebicin M (kvarM), or a variant having at least 50% sequence identity to Klebicin M (SEQ ID NO: 21).

In an embodiment, the bacteriophage is derived from wild-type bacteriophage *Enterococcus* phage Efs3 and the bacteriocin is Colicin M, or a variant having at least 50% sequence identity to Colicin M (SEQ ID NO: 18).

In an embodiment, the bacteriophage is derived from wild-type bacteriophage *Enterococcus* phage Efs3 and the bacteriocin is Colicin E7, or a variant having at least 50% sequence identity to Colicin E7 (SEQ ID NO: 20).

In an embodiment, the bacteriophage is derived from wild-type bacteriophage *Enterococcus* phage Efs3 and the bacteriocin is Colicin E6, or a variant having at least 50% sequence identity to Colicin E6 (SEQ ID NO: 16).

In an embodiment, the bacteriophage is derived from wild-type bacteriophage *Enterococcus* phage Efs3 and the bacteriocin is Colicin K, or a variant having at least 50% sequence identity to Colicin K (SEQ ID NO: 19).

In an embodiment, the bacteriophage is derived from wild-type bacteriophage *Enterococcus* phage Efs3 and the bacteriocin is Colicin 5, or a variant having at least 50% sequence identity to Colicin (SEQ ID NO: 17).

In an embodiment, the bacteriophage is derived from wild-type bacteriophage *Enterococcus* phage Efs3 and the bacteriocin is Klebicin M (kvarM), or a variant having at least 50% sequence identity to Klebicin M (SEQ ID NO: 21).

In an embodiment, the bacteriophage is derived from wild-type bacteriophage *Enterococcus* phage Efs7 and the bacteriocin is Colicin M, or a variant having at least 50% sequence identity to Colicin M (SEQ ID NO: 18).

In an embodiment, the bacteriophage is derived from wild-type bacteriophage *Enterococcus* phage Efs7 and the bacteriocin is Colicin E7, or a variant having at least 50% sequence identity to Colicin E7 (SEQ ID NO: 20).

In an embodiment, the bacteriophage is derived from wild-type bacteriophage *Enterococcus* phage Efs7 and the bacteriocin is Colicin E6, or a variant having at least 50% sequence identity to Colicin E6 (SEQ ID NO: 16).

In an embodiment, the bacteriophage is derived from wild-type bacteriophage *Enterococcus* phage Efs7 and the bacteriocin is Colicin K, or a variant having at least 50% sequence identity to Colicin K (SEQ ID NO: 19).

In an embodiment, the bacteriophage is derived from wild-type bacteriophage *Enterococcus* phage Efs7 and the bacteriocin is Colicin 5, or a variant having at least 50% sequence identity to Colicin (SEQ ID NO: 17).

In an embodiment, the bacteriophage is derived from wild-type bacteriophage *Enterococcus* phage Efs7 and the bacteriocin is Klebicin M (kvarM), or a variant having at least 50% sequence identity to Klebicin M (SEQ ID NO: 21).

In an embodiment, the bacteriophage is derived from wild-type bacteriophage *E. coli* phage phi41S and the bacteriocin is Colicin M, or a variant having at least 50% sequence identity to Colicin M (SEQ ID NO: 18).

In an embodiment, the bacteriophage is derived from wild-type bacteriophage *E. coli* phage phi41S and the bacteriocin is Colicin E7, or a variant having at least 50% sequence identity to Colicin E7 (SEQ ID NO: 20).

In an embodiment, the bacteriophage is derived from wild-type bacteriophage *E. coli* phage phi41S 1 and the bacteriocin is Colicin E6, or a variant having at least 50% sequence identity to Colicin E6 (SEQ ID NO: 16).

In an embodiment, the bacteriophage is derived from wild-type bacteriophage *E. coli* phage phi41S and the bacteriocin is Colicin K, or a variant having at least 50% sequence identity to Colicin K (SEQ ID NO: 19).

In an embodiment, the bacteriophage is derived from wild-type bacteriophage *E. coli* phage phi41S and the bacteriocin is Colicin 5, or a variant having at least 50% sequence identity to Colicin 5 (SEQ ID NO: 17).

In an embodiment, the bacteriophage is derived from wild-type bacteriophage *E. coli* phage phi41S and the bacteriocin is Klebicin M (kvarM), or a variant having at least 50% sequence identity to Klebicin M (SEQ ID NO: 21).

In the embodiments herein, the modified bacteriophage may be a bacteriophage having a genome that has at least 50% sequence identity to a sequence as set forward in SEQ ID NO: 6-15, 23-31 or 33.

The modified bacteriophage as defined in the embodiments herein can conveniently be comprised in a composition.

Accordingly, in a second aspect there is provided for a composition comprising a carrier and a modified bacteriophage as defined in the first aspect. The carrier may be any carrier known to the person skilled in the art. In the embodiments herein, the composition will typically comprise water and a modified bacteriophage as defined in the first aspect. Other components may be present that are known in the field of bacteriophages such as a buffering agent and a preservation agent.

In the embodiments herein, the composition may be a pharmaceutical composition. Such composition fulfils the requirements for pharmaceutical use and may comprise a pharmaceutical grade excipient and/or a further active ingredient.

In the embodiments herein, the composition may be formulated to contain specific excipients known to the person skilled in the art to allow any specific route of administration; the composition may be formulated for topical, intravenous, intramuscular, intrathecal, oral, intraperitoneal, vaginal, rectal, lumbar, or meningeal administration.

The bacteriophage as defined in the first aspect and the composition as defined in the second aspect may conveniently be used for antibacterial decontamination.

Accordingly, in a third aspect there is provided for the use of a modified bacteriophage as defined in the first aspect or of a composition as defined in the second aspect, for in vitro or ex vivo antibacterial decontamination. The product to be contaminated may be any product where decontamination is required, such as but not limited to food processing equipment, food products, medical devices, and surfaces in a hospital such as in an operation room.

The bacteriophage as defined in the first aspect and the composition as defined in the second aspect may conveniently be used for detection of a bacterial pathogen.

Accordingly, there is provided for the use of a modified bacteriophage as defined in the first aspect or of a composition as defined in the second aspect, for in vitro or ex vivo detection of a bacterial pathogen.

The bacteriophage as defined in the first aspect and the composition as defined in the second aspect may conveniently be used for treatment of bacterial infections in subject in need thereof.

Accordingly, in a fourth aspect, there is provided for a modified bacteriophage as defined in the first aspect or a composition as defined in the second aspect, for use as a medicament for the treatment of a bacterial infection in a subject in need thereof.

Further provided is the use of a modified bacteriophage as defined in the first aspect or of a composition as defined in the second aspect, for the production of a medicament for the treatment of a bacterial infection in a subject in need thereof.

Further provided is a method of treatment of a bacterial infection in a subject in need thereof, comprising administration of a therapeutically effective amount of a modified bacteriophage as defined in the first aspect or of a composition as defined in the second aspect, to the subject, thereby treating the bacterial infection.

In the embodiments herein, a therapeutically active amount is defined as such amount that decreases the amount of the target bacterium present in the subject by preferably 100%, 99%, 90%, 80%, 70%, 60%, 50%, 40%, 30%, 20%, 10%, or at least 5%.

The subject may be an animal, preferably a mammal and more preferably a human.

The bacteriophage or composition may be administered in any way known to the person skilled in the art, preferably one of the routes described elsewhere herein.

The bacteriophage as defined in the first aspect and the composition as defined in the second aspect may conveniently be used for altering the microbial composition of a microbiome.

Accordingly, in a further aspect there is provided for a method of altering the microbial composition of a microbiome, comprising introducing a modified bacteriophage as defined in the first aspect or a composition into the second aspect into the microbiome. The microbiome may be present in a subject or may be an in vivo or ex vivo microbiome.

TABLE 1

| | Overview of sequences | |
|---|---|---|
| SEQ ID NO: | Identity | Host/target organism |
| 1 | Wild-type K1 phage | *Klebsiella* |
| 2 | Wild-type CM001 phage | *E. coli* |
| 3 | Wild-type phage Efs3 | *Enterococcus* |
| 4 | Wild-type phage Efs7 | *Enterococcus* |
| 5 | Wild-type E2 phage | *E. coli* |
| 6 | K1_kvarM | *Klebsiella* |
| 7 | CM001_colE7 | *E. coli* |
| 8 | Efs3_kvarM | *Enterococcus* |
| 9 | Efs3_colE7 | *Enterococcus* |
| 10 | Efs7_kvarM | *Enterococcus* |
| 11 | K1_colM | *Klebsiella* |
| 12 | K1_colE6 | *Klebsiella* |
| 13 | Efs3_colM | *Enterococcus* |
| 14 | Efs7_colM | *Enterococcus* |
| 15 | E2_colE7 | *E. coli* |
| 16 | colE6 | *E. coli* (target) |
| 17 | col5 | *E. coli* (target) |
| 18 | colM | *E. coli* (target) |
| 19 | colK | *E. coli* (target) |
| 20 | colE7 | *E. coli* (target) |
| 21 | KvarM | *Klebsiella* (target) |
| 22 | Wild-type phi41S phage | *E. coli* |
| 23 | E2_col5 | *E. coli* |
| 24 | E2_KvarM | *E. coli* |
| 25 | Efs3_colE7 | *Enterococcus* |
| 26 | Efs7_colE7 | *Enterococcus* |
| 27 | K1_col5 | *Klebsiella* |
| 28 | K1-colE7 | *Klebsiella* |
| 29 | K1_colK | *Klebsiella* |
| 30 | phi41S_col5 | *E. coli* |
| 31 | phi41S_coE7 | *E. coli* |
| 32 | EC300 | *Enterococcus* (target) |
| 33 | CM001_ec300 | *E. coli* |

Graphical representation of bacteriophages engineered to encode and produce bacteriocins as genetic payloads. Graphical representation generated with BioRender.

Figure 2A:
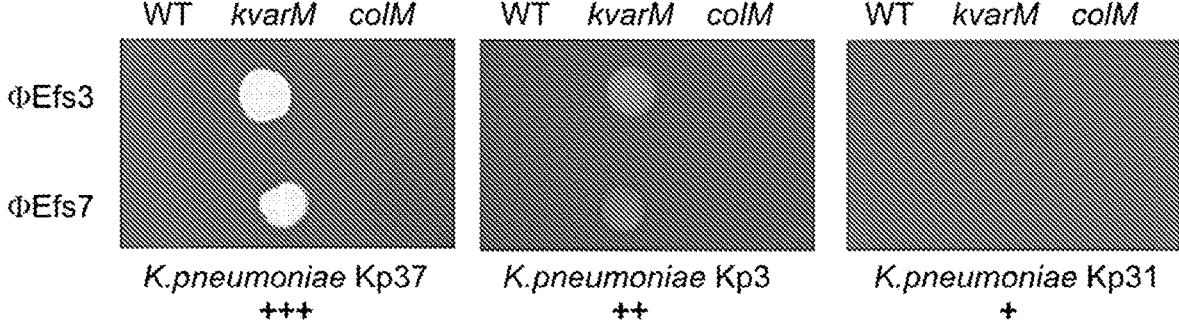

FIG. 2A-2B. Engineered phages produce active bacteriocins.

Phage lysates were spotted on bacterial lawns using the soft-agar overlay method and incubated over-night at 37° C. Growth inhibition/antibacterial effect were scored as shown in (FIG. 2A) using Klebicin M and Colicin M-producing

*Enterococcus* phages as examples. Bacteriocin production and activity on urological *E. coli* and *Klebsiella* isolates is summarized in (FIG. 2B).

Figure 3A:
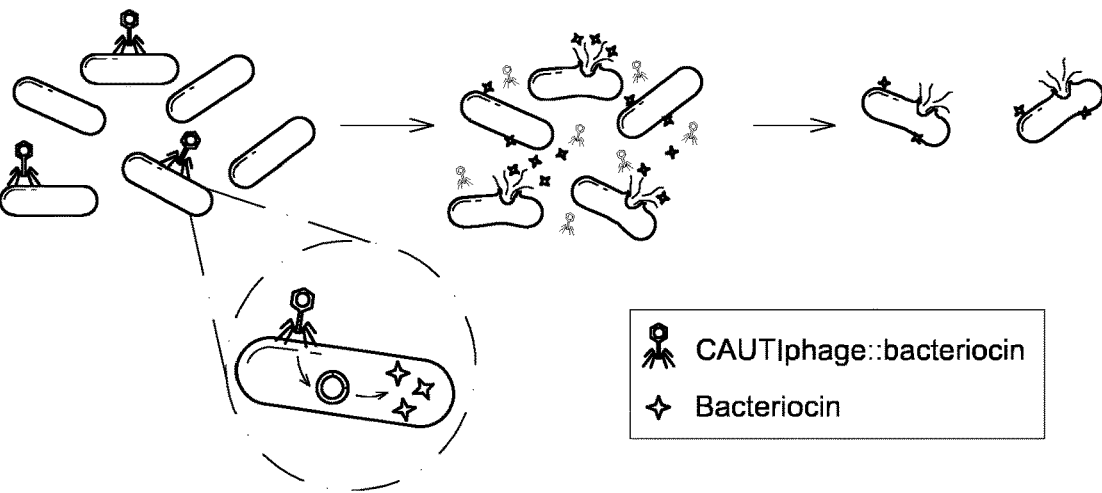
Figure 3B:
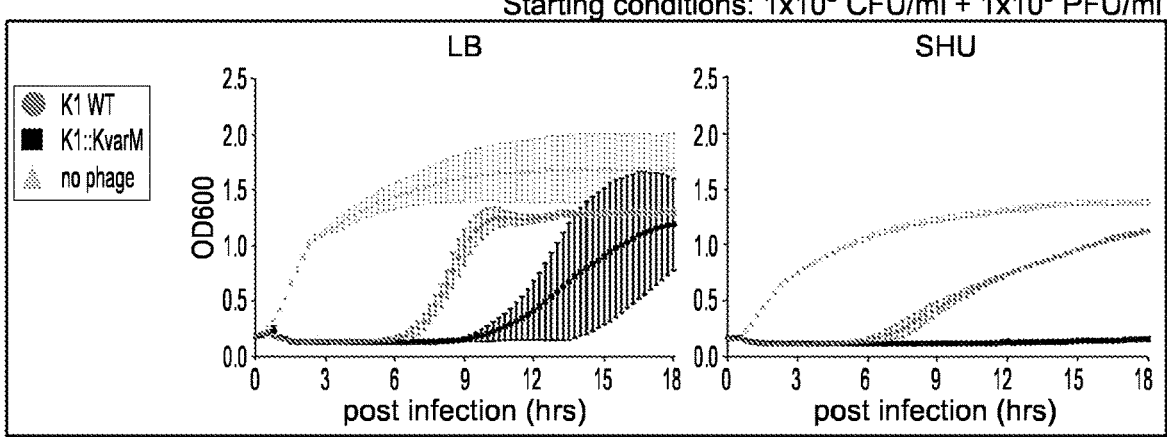
Figure 3C:
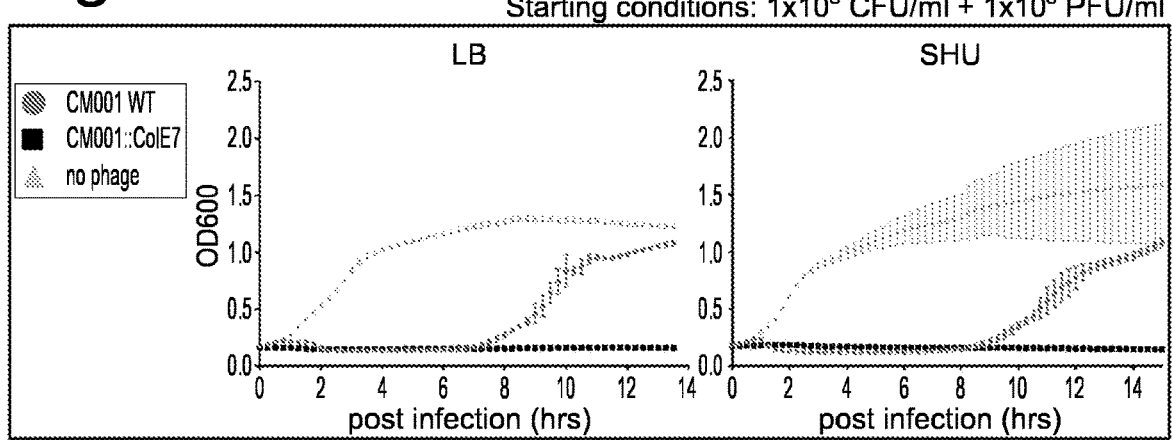

FIG. 3A, 3B, 3C. Enhanced host-killing by bacteriocin-producing phages.

(FIG. 3A) Resistant sub-populations are targeted during phage infection through the release of phage-encoded bacteriocins. While the wild type phages K1 and CM001 can only control bacterial growth for 6 to 9 hours before host cells start to overgrow the culture, the engineered Klebicin M and Colicin E7-producing bacteriophages are able to prevent or delay regrowth of *Klebsiella* (FIG. 3B) and *E. coli* (FIG. 3C) in both LB and SHU media. CFU=colony forming unit; PFU=plaque forming unit.

Figures 4A, 4B:
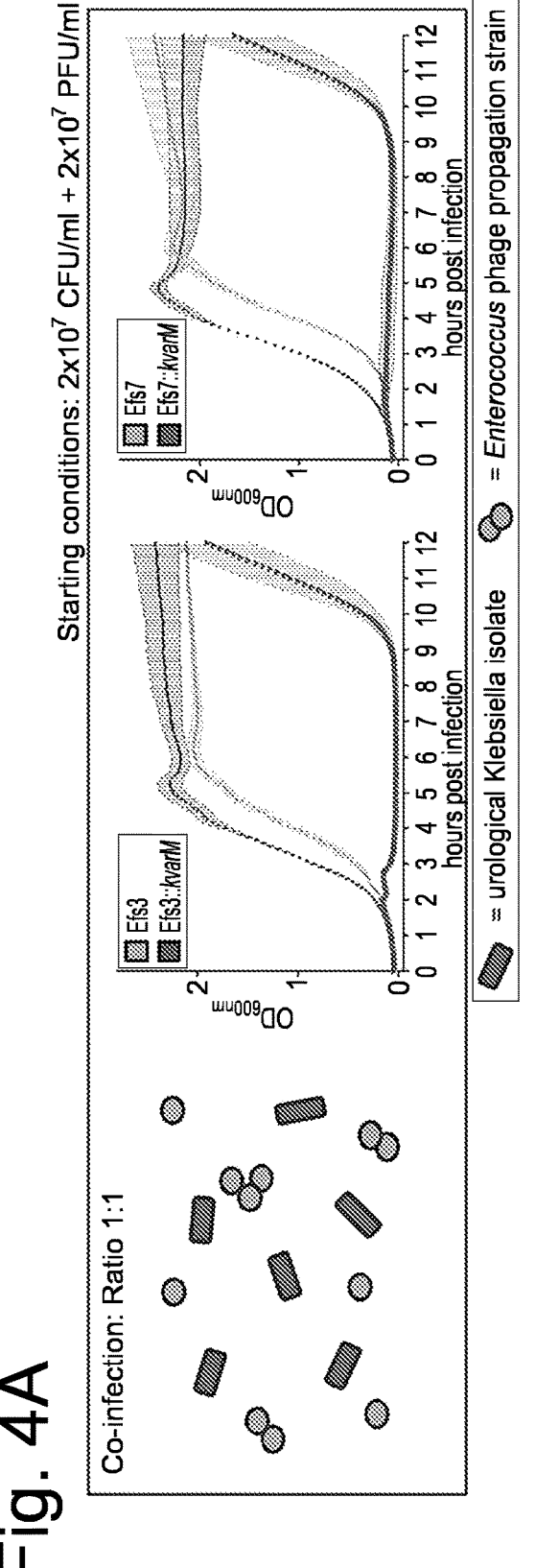

FIG. 4A-4B. Klebicin M-producing *E. faecalis* phages are able to clear *Enterococcus/Klebsiella* co-cultures.

*E. faecalis* and urological *K. pneumoniae* isolates were co-cultured at a ratio of 1:1 (FIG. 4A) or 100:1 cells (FIG. 4B), infected with wt or kvarM-encoding *Enterococcus* phages using the indicated starting conditions, and $OD_{600\ nm}$ was followed for 12 hours post infection at 30° C.

Figures 5A, 5B:
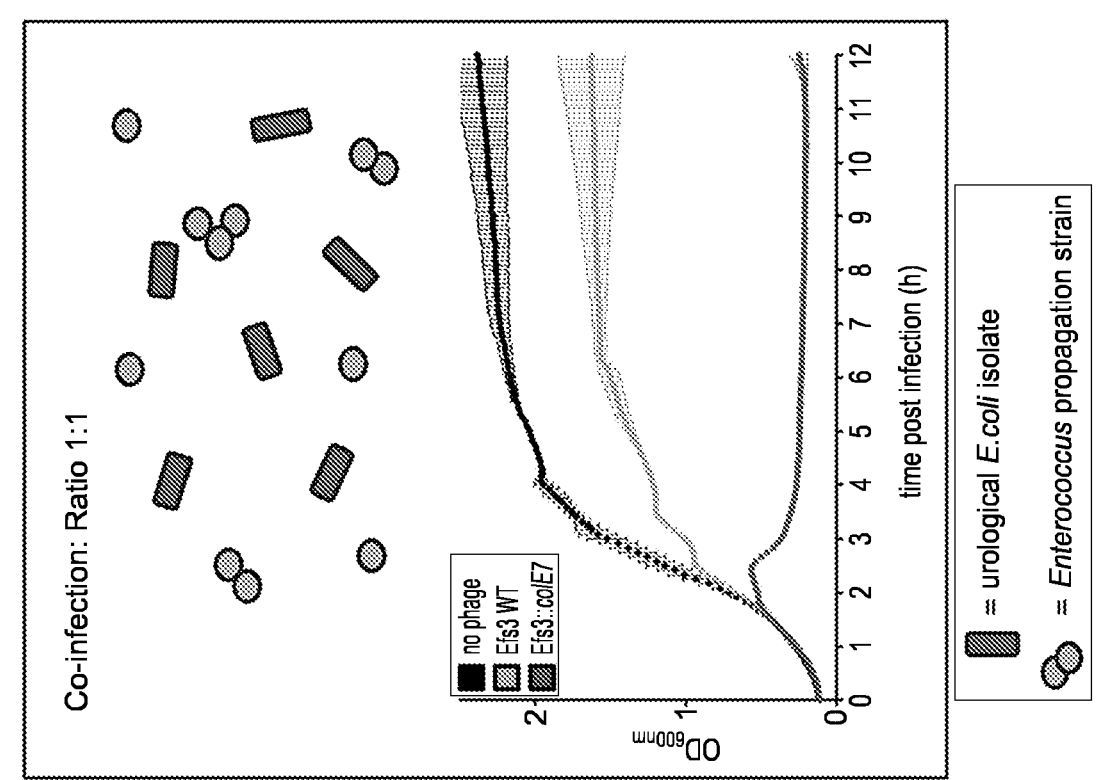

FIG. 5A-5B. Colicin E7-producing *E. faecalis* phages are able to clear *Enterococcus/E. coli* co-cultures.

*E. faecalis* and urological *E. coli* isolates were co-cultured at a ratio of 1:1 (FIG. 5A) or 10:1 cells (FIG. 5B), infected with wt or co/E7-encoding Efs3 phage, and $OD_{600\ nm}$ was followed for 12 hours post infection at 30° C.

FIG. 6A, 6B, 6C, 6D, 6E, 6F, 6G, 6H. Cross-targeting HEPTs control polymicrobial uropathogen communities.

(FIG. 6A) Heterologous effector phage therapeutics (HEPTs) enable pathogen-specific delivery and production of antimicrobial effector genes (yellow). Upon phage-induced host cell lysis, effectors are released alongside progeny virions to exert a secondary antimicrobial activity against defined bacterial targets. HEPTs were designed against the uropathogens *E. coli* (light green), *K. pneumoniae* (light purple), and *E. faecalis* (light blue).

(FIG. 6B) Five phages were employed as HEPT scaffolds to integrate colicins (M, E6, and E7; square star), klebicin M (star), or the *E. faecalis*-specific cell wall hydrolase EC300 (Pac-Man) (28) within the phage structural gene cassette.

Figure 6A:
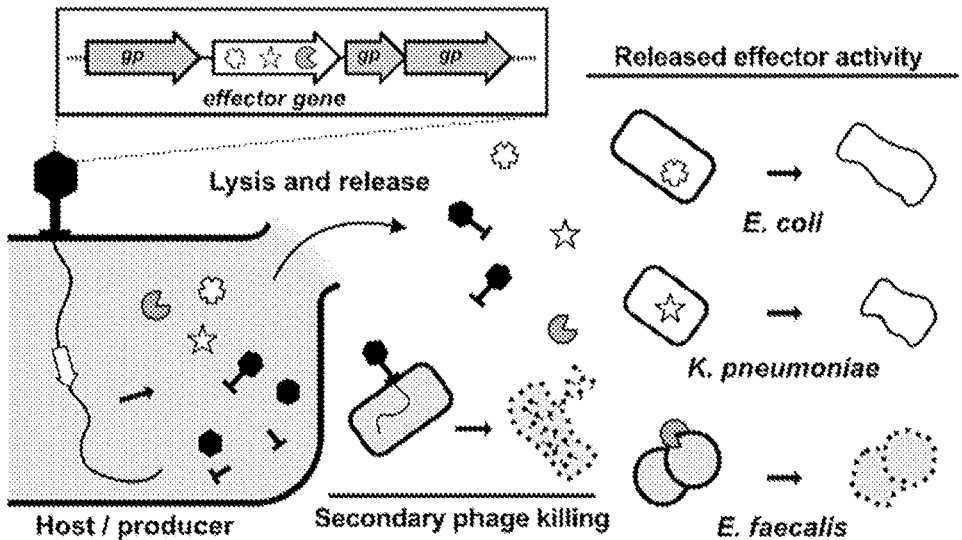
Figure 6B:
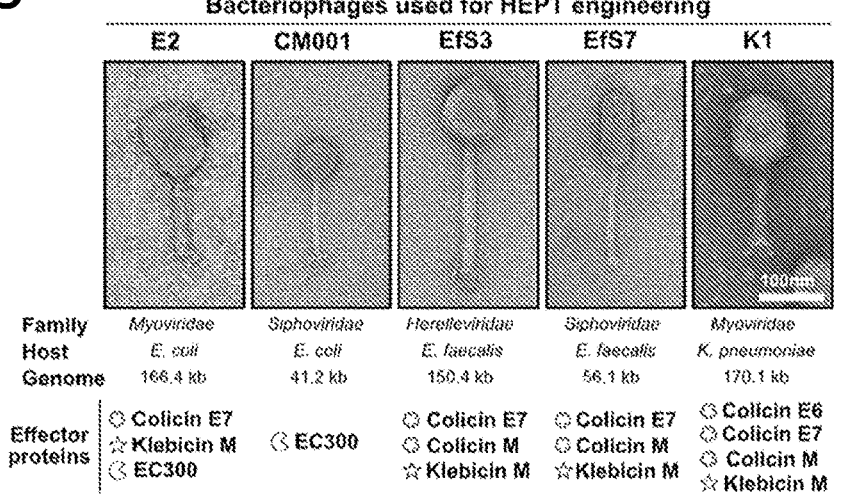
Figure 6C:
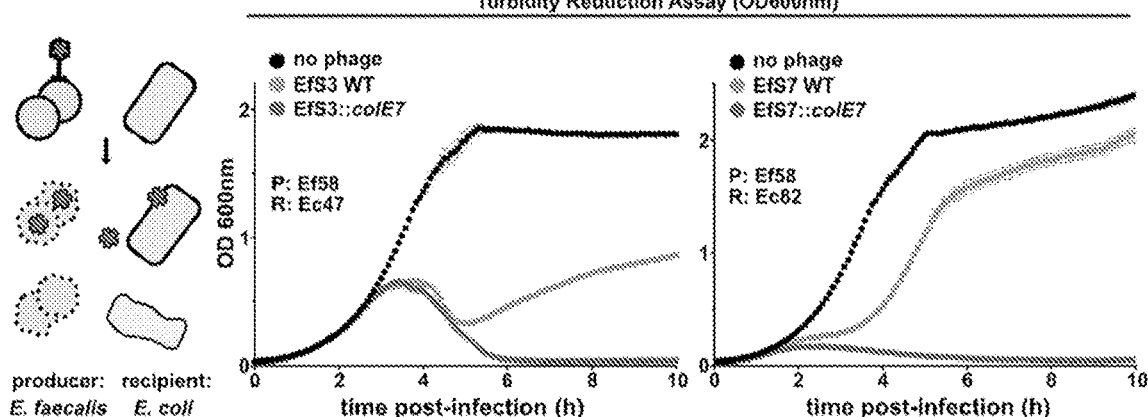
Figure 6D:
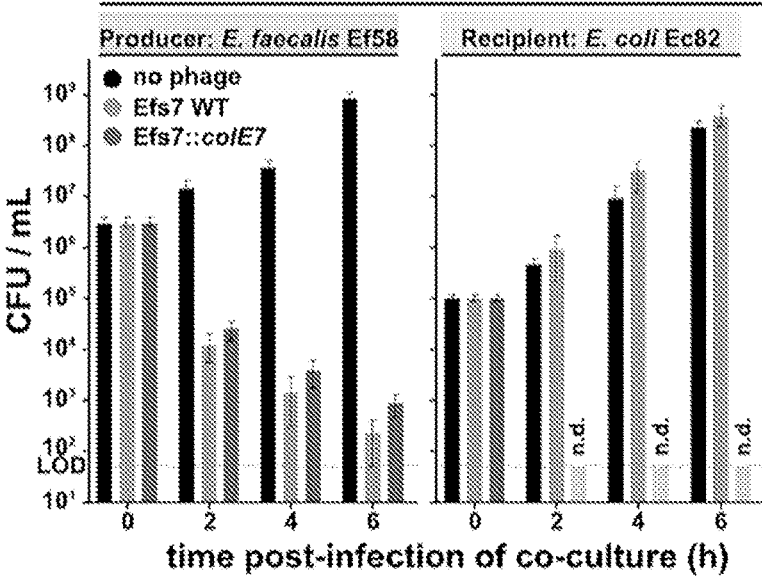
Figure 6E:
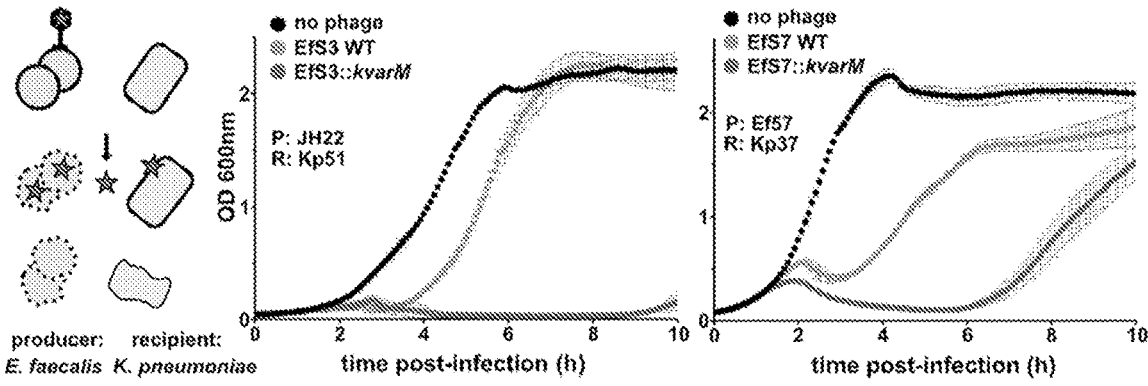
Figure 6F:
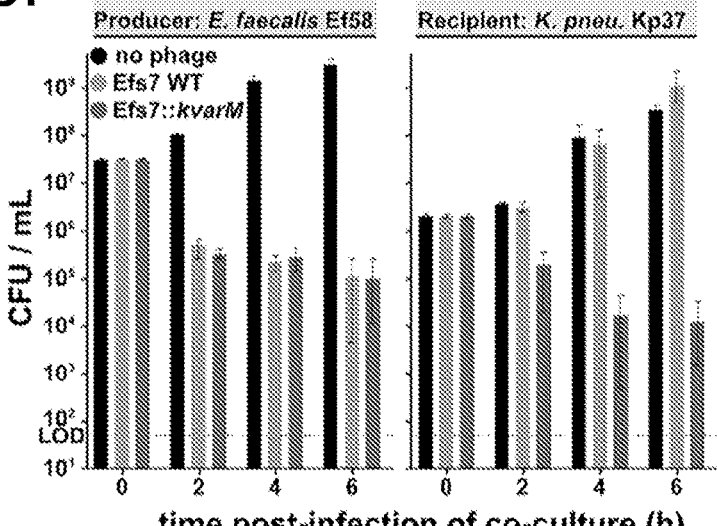
Figure 6G:
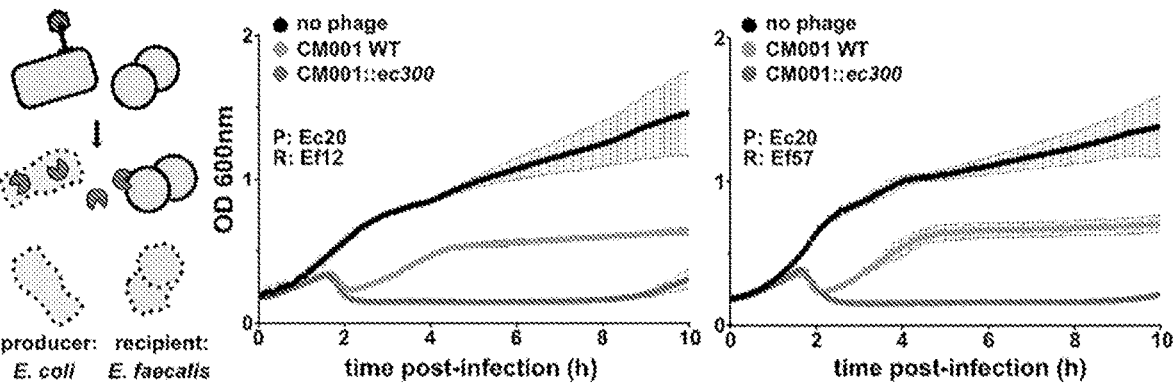
Figure 6H:
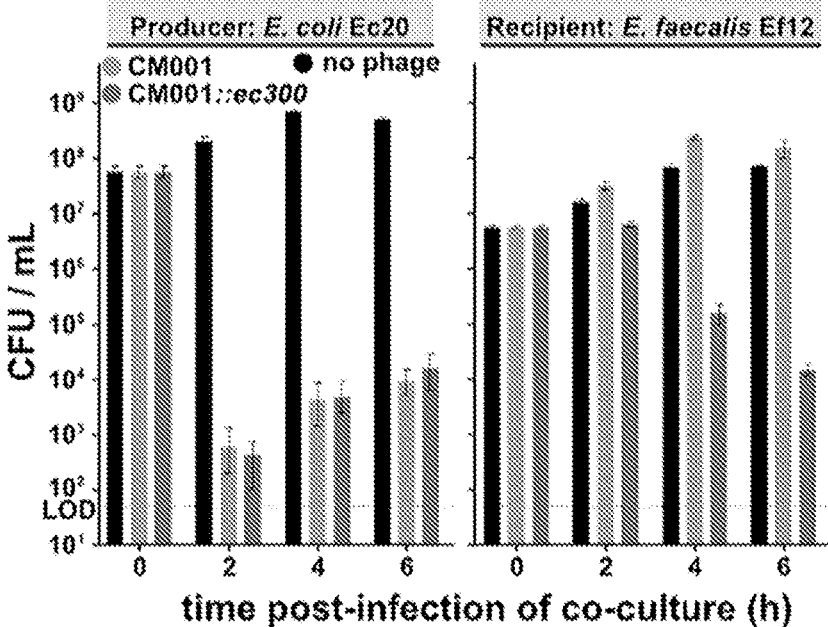

(FIG. 6C, 6D, 6E, 6F, 6G, 6H) The colour of the effector symbol matches the target organism. The antimicrobial effect of cross-targeting HEPTs was compared to their WT counterparts upon infecting co-cultures of a phage-susceptible host (P, producer) and an effector-susceptible target (R, recipient). Bacterial killing was quantified using 10 h turbidity reduction assays (FIG. 6C, FIG. 6E, FIG. 6G). 6 h time kill assays were combined with plating on differential and selective agar to enumerate different bacterial species (FIG. 6D, FIG. 6F, FIG. 6H). Strains used from the Zurich Uropathogen Collection: *E. faecalis* Ef12/57/58; *E. coli* Ec20/47/82; *K. pneumoniae* Kp37/51; gp=gene product; LOD=limit of detection; $OD_{600\ nm}$=optical density at 600 nm. Data are shown as mean±SD (n=3).

FIG. 7A-7B-7C-7D. Self-targeting HEPTs enhance killing of uropathogenic *E. coli* and *K. pneumoniae* isolates through release of colicin-like bacteriocins.

(FIG. 7A) The rapid propagation of bacteria (pink) surviving WT phage treatment (e.g., phage-resistant or tolerant subpopulations) results in a failure to control bacterial growth. Self-targeting HEPTs can prevent or delay the growth of resistant subpopulations in vitro by releasing complementary antimicrobial effectors.

(FIG. 7B) Genes encoding colicin E7 (green) or klebicin M (purple) were integrated within the structural gene cassette of phage scaffolds E2 or K1 to generate HEPTs targeting *E. coli* (E2::colE7) or *K. pneumoniae* (K1::kvarM).

(FIG. 7C-FIG. 7D) Turbidity reduction assays combined with timepoint plating (red stars) demonstrated improved antimicrobial activity (i.e., regrowth was avoided or delayed) for E2::colE7 (FIG. 7C) and K1::kvarM (FIG. 7D) compared to WT phage treatment of uropathogenic *E. coli* and *K. pneumoniae* monocultures, respectively. hoc=highly immunogenic outer capsid protein. HEPTs=heterologous effector phage therapeutics, CLB=colicin-like bacteriocin. $OD_{600\ nm}$=optical density at 600 nm. Data are shown as mean±SD (n=3).

Figure 8C:
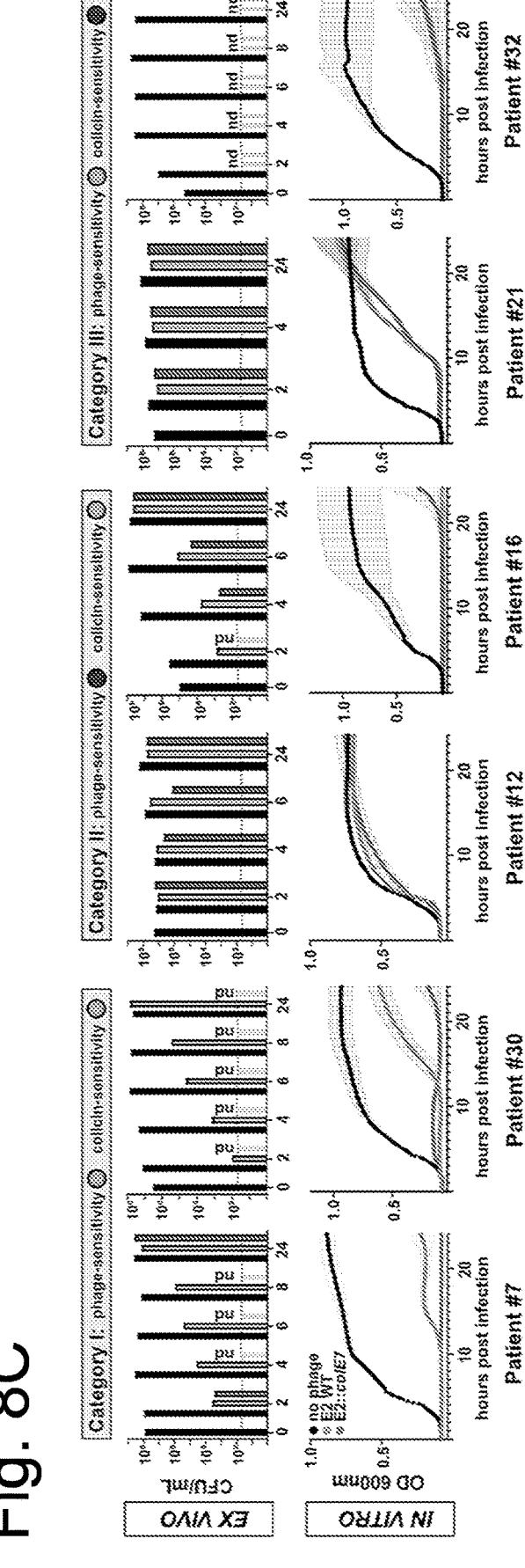

FIG. 8A-8B-8C. HEPTs provide enhanced killing of colicin-sensitive *E. coli* in patient urine. (FIG. 8A) Workflow for combining a phage-based companion diagnostic to identify potential HEPT responder patients presenting with E2-sensitive *E. coli* bacteriuria (steps 1-2) with subsequently ex vivo treatment (step 3) and in vitro assessment (step 4) of positive urine specimens using E2 WT or E2::colE7.

(FIG. 8B) Patient urine samples (n=39) were subjected to a bioluminescence-based (E2::nluc) reporter phage assay (3) to identify E2-sensitive *E. coli* in the urine within 4.5 h (3). Urine was plated on differential agar to isolate patient strains and enumerate overall bacterial load. *E. coli* isolates were further tested in vitro for E2 sensitivity (plaque formation) and colicin E7 sensitivity (detailed results provided in FIG. 13) and categorized: Category I=phage and colicin sensitive; Category II=phage-resistant, colicin-sensitive; Category III=phage-sensitive, colicin-resistant.

(FIG. 8C) Time kill assays were used to assess ex vivo treatment using $10^9$ PFU/mL E2 or E2::colE7 added to fresh urine for 24 h at 37° C. A similar HEPT treatment was performed in vitro on patient isolates grown in SHU with bacterial killing measured using turbidity reduction assays. $OD_{600\ nm}$=optical density at 600 nm. Turbidity data is mean±SD (n=3). *, specimen #5 was excluded due to a *K. pneumoniae* polymicrobial infection.

Figure 9A:
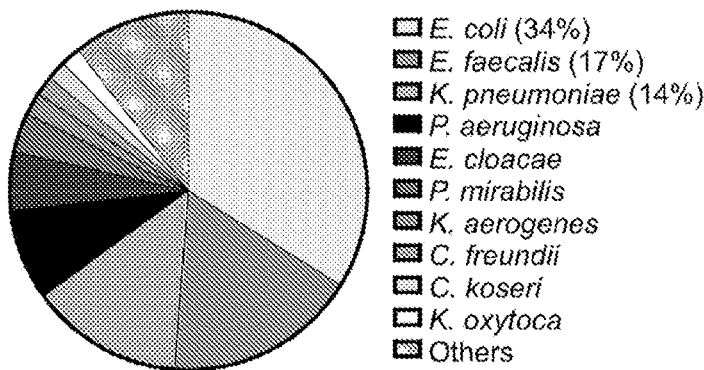
Figure 9B:
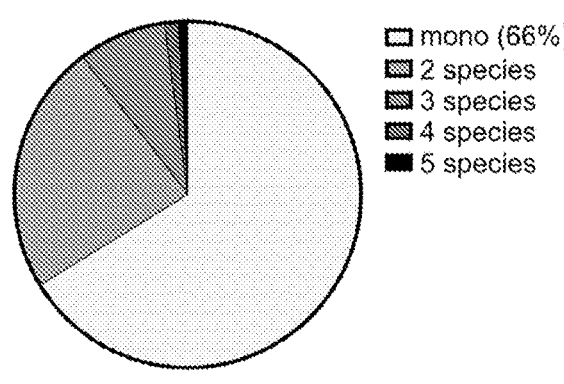
Figure 9C:
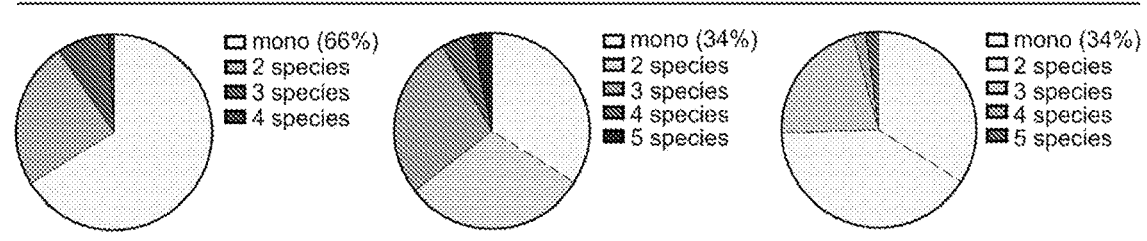

FIG. 9A-9B-9C. Analysis of UTI incidents within the Zurich Uropathogen Collection.

The Zurich Uropathogen Collection comprises 665 isolates from 461 incidents of asymptomatic bacteriuria (n=230) or UTI (n=231).

(FIG. 9A) The species distribution of 340 isolates acquired from UTI patients was determined and (FIG. 9B) the occurrence of mono- vs polymicrobial infections quantified for the corresponding UTI incidents.

(FIG. 9C) UTI incidents involving the top three uropathogens were analyzed separately to determine the top five co-infecting species and the frequency of mono- and polymicrobial UTIs.

FIG. 10. HEPT construction and assessment of payload activities. (A): Codon-optimized genes encoding for colicins (M, E6, and E7, green), klebicin M (purple), or the *E. faecalis*-specific cell wall hydrolase EC300 (blue) (8) were integrated within the structural gene cluster of the corresponding phage scaffold alongside a strong ribosomal binding site (RBS) to mediate phage promoter-driven effector expression.

(B-D): Cross-genus antimicrobial activity of crude WT phage or HEPT lysates were tested using the spot-on-the-lawn method against clinical uropathogen isolates. cps, major capsid protein; gp, gene product; hoc, highly immunogenic outer capsid protein; 168, phage K1 gene product 168; kb, kilobase; HEPTs, heterologous effector phage therapeutics.

FIG. 11A-11B. Simultaneous application of two cross- or two self-targeting HEPTs to co-cultures containing uropathogenic *E. coli* and *K. pneumoniae*.

Growing cultures of *E. coli* (Ec41) and *K. pneumoniae* (Kp37) were adjusted to $OD_{600\ nm}$ of 0.1, mixed at a ratio of 1:1, and infected with the indicated WT phages and/or HEPTs ($5\times10^7$ PFU/mL). Optical density was monitored over 18 h of infection at 30° C., followed by differential plating on chromogenic coliform agar (matching box and curve colors). Double cross-targeting with phages E2::kvarM and K1::colE7 was assessed in (FIG. 11A), while double self-targeting with phages E2::colE7 and K1::kvarM was assessed in (FIG. 11B). P, producer; R, recipient; HEPTs, heterologous effector phage therapeutics. Data is mean±SD (n=3).

Figures 12C, 12D:
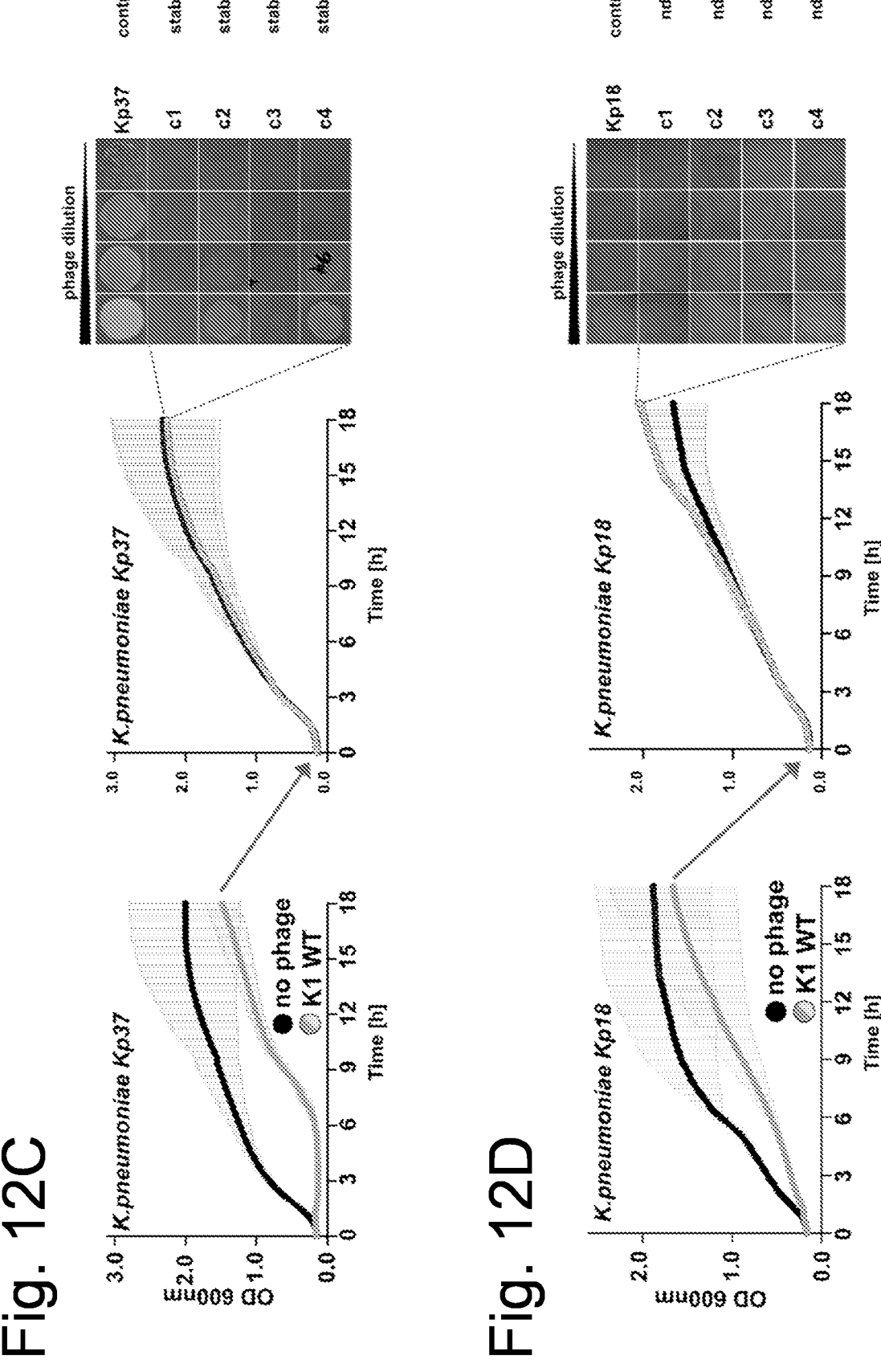
Figure 12E:
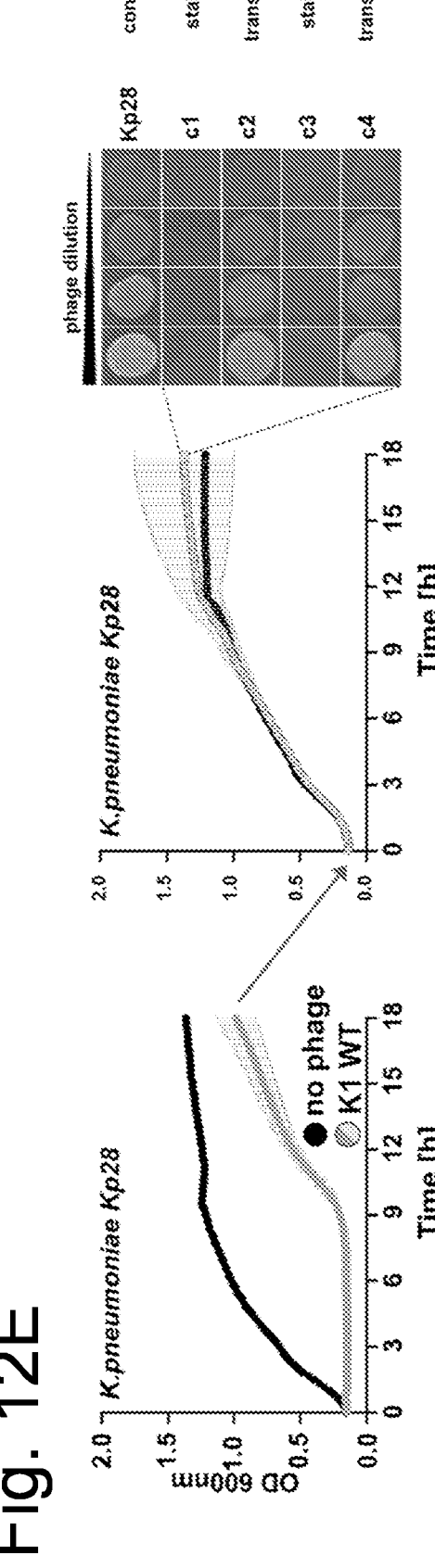

FIG. 12. Phage resistance development upon treatment of UTI isolates with wildtype E2 and K1.

Phage resistance development was assessed by two consecutive rounds of phage infection of bacterial cultures in SHU medium. Turbidity reduction assays were performed for *E. coli* isolates Ec20 (A) and Ec41 (B) or *K. pneumoniae* isolates Kp37 (C) and, Kp18 (D), and Kp28 (E) infected with $10^8$ PFU/mL of phages E2 or K1, respectively, with optical density monitored for 18 h. Phage-exposed cultures were combined (n=3), re-adjusted to $OD_{600\ nm}$ of 0.1 in SHU and incubated for another 18 h with additional wildtype (WT) phages (pink) or media alone (black). Growth kinetics were compared to non-infected controls. After the second round of infection, individual clonal survivors were isolated (three rounds of colony purification) and assessed for phage susceptibility using spot-on-the-lawn assays. Turbidity data is mean±SD (n=3). nd=not determined.

Figure 13A:
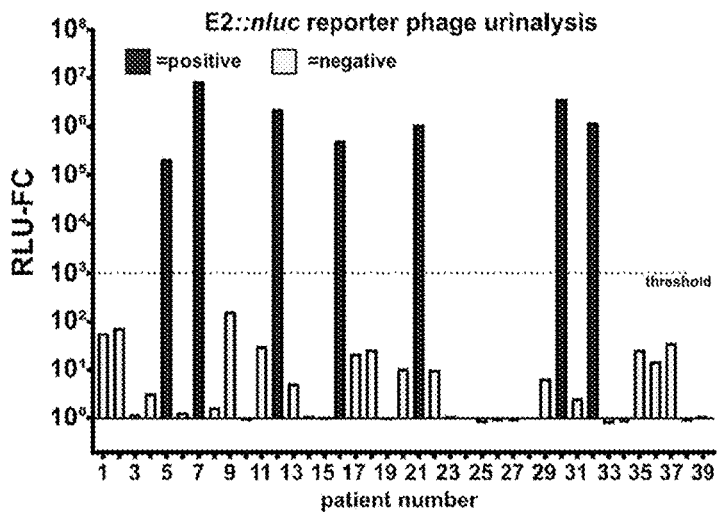
Figure 13B:
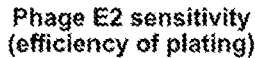
Figure 13C:
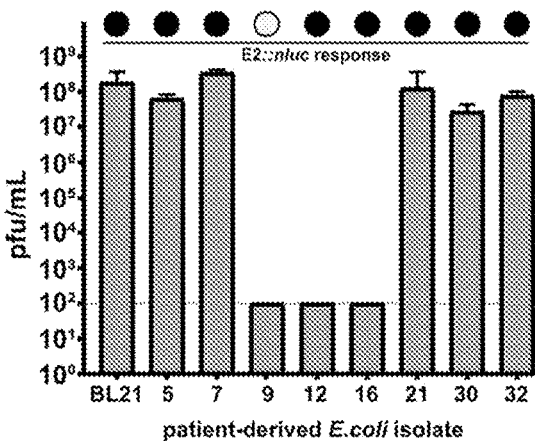
Figure 14A:
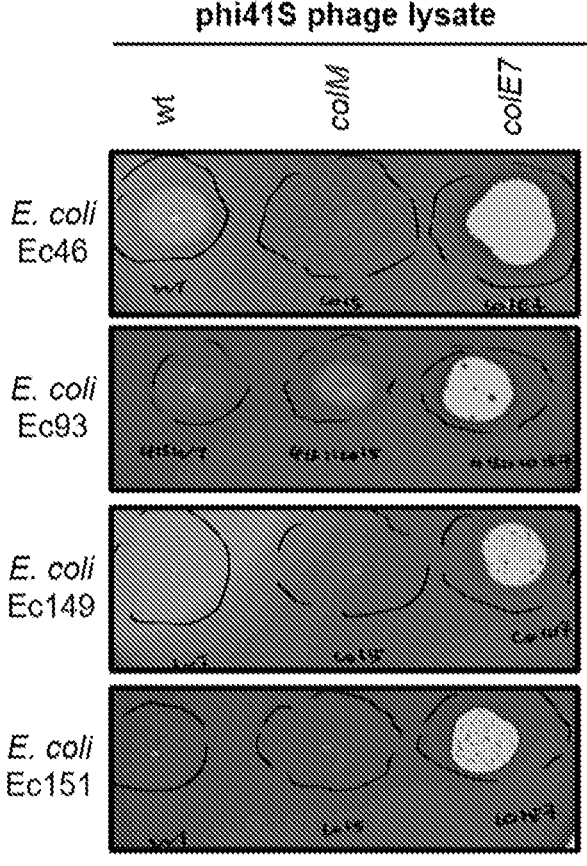
Figure 14B:
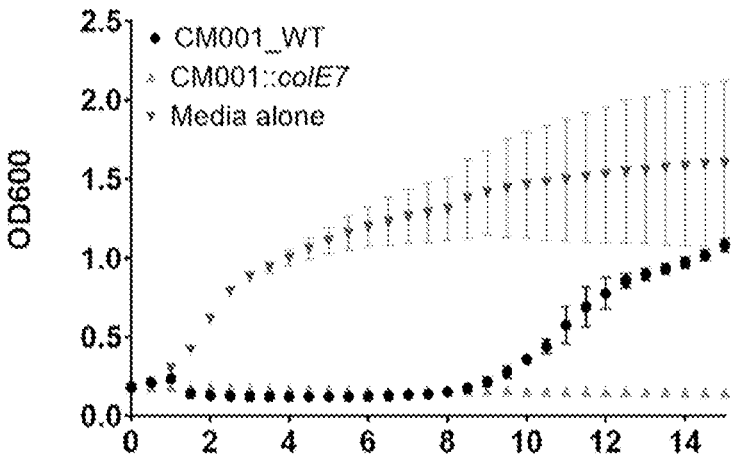

FIG. 13A-13B-13C. Reporter phage-based urinalysis of patient urine samples with phage and colicin E7 susceptibility screening of isolated, patient-derived *E. coli* strains.

(FIG. 13A) Reporter phage urinalysis was performed using 39 fresh patient urine samples from the Balgrist University Hospital, Zurich, Switzerland, as described in the Materials and Methods and in (1). The fold change (compared to media alone) in relative light units (RLU-FC) was determined at 3 hours post-infection with urine samples producing values $>10^3$ considered as positive samples, i.e., containing E2-susceptible *E. coli*.

(FIG. 13B) All *E. coli* strains were isolated and purified from patient urine after differential plating, and E2-susceptibility quantified using plaque assays (efficiency of plating).

(FIG. 13C) Colicin E7 effector susceptibility was determined on patient-derived *E. coli* strains by spotting K1 WT or K1::colE7 phage lysates.

FIG. 14A-14B-14C-14D-14E. Spot assays and turbidity reduction assays of additional self-targeting HEPTs.

(FIG. 14A) Activity of phi41S wildtype and phi41S-derived HEPTS that produce colicin M (phi41S::colM) or colicin E7 (phi41S::colE7) was assessed by spot-on-the-lawn assays. In short, crude phage lysates were generated by infection of the phi41S propagation host (*E. coli* Ec20) to produce semi-confluent lysis on agar plates. Phages (and produced bacteriocin payload) were extracted with 5 mL SM buffer (2 h, 4° C.) and sterile filtered (0.22 mM). Resulting lysates were spotted on growing bacteria lawns (grey) of the indicated strains. Activity of phage and/or payload is visualized through reduced turbidity on the spot-area. Wildtype phage lysates served as a control. (FIG. 14B-14C-14D-14E) Turbidity reduction assays were performed with the indicated self-targeting HEPTs and wildtype phage controls. Bacterial cultures were diluted to $5\times10^7$ CFU/mL in synthetic human urine (SHU) and infected with $5\times10^7$ PFU/mL of the indicated phage in 96-well plates at 37° C. and the optical density at 600 nm (OD600) was monitored over time. Uninfected bacterial cultures served as a growth control (Media alone). Data is mean±SD. All *E. coli* strains are clinical isolates from the Zurich Uropathogen Collection. co/M=colicin M gene; colE7=colicin E7 gene; col5=colicin 5 gene.

Figure 15A:
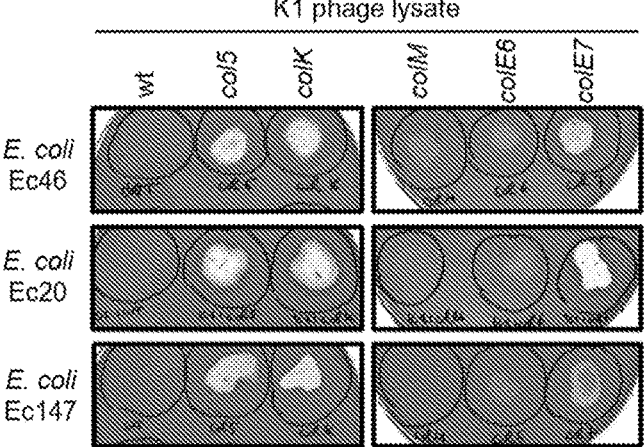
Figure 15B:
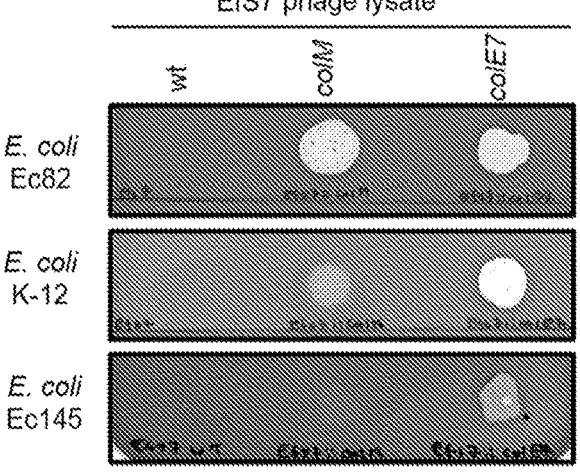
Figure 15C:
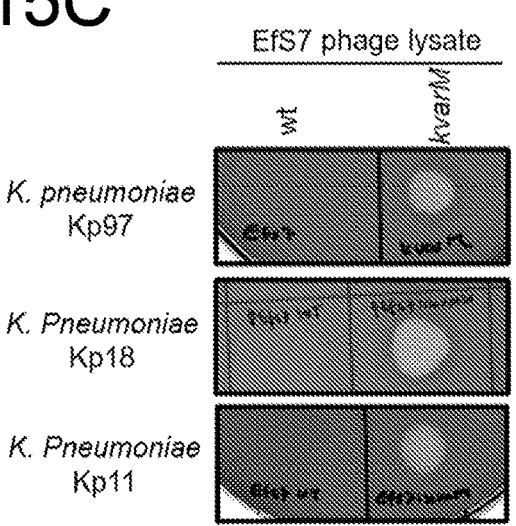

FIG. 15A-15B-15C. Spot assays of additional cross-genus targeting HEPTs. Activity of engineered HEPTs producing bacteriocins with cross-genus activity was assessed by spot-on-the-lawn assays. In short, crude phage lysates were generated by infection of the propagation host to produce semi-confluent lysis on agar plates. Phages (and produced bacteriocin payload) were extracted with 5 mL SM buffer (2 h, 4° C.) and sterile filtered (0.22 mM). Resulting lysates were spotted on growing bacteria lawns (grey) of the indicated strains. Activity of payload is visualized through reduced turbidity on the spot-area. Wildtype phage lysates served as a control. FIG. 15A Bacteriocin activity of lysates from *K. pneumoniae* phages K1 wildtype, K1::col5, K1::colK, K1::colE6, and K1::colE7 on several clinical *E. coli* isolates. (FIG. 15B. FIG. 15C) Bacteriocin activity of lysates from *E. faecalis* phages EfS7 wildtype, EfS7::co/M, EfS7::co/E7, and EfS7::kvarM on several clinical *E. coli* or *K. pneumoniae* isolates. col5=colicin 5 gene; colK=colicin K gene; colM=colicin M gene; colE6=colicin E6 gene; colE7=colicin E7 gene, kvarM=klebicin M gene. Except for *E. coli* K-12, all tested strains are from the Zurich Uropathogen Collection.

DEFINITIONS

"Sequence identity" is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. "Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, MD 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, WI. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A "nucleic acid molecule" or "polynucleotide" (the terms are used interchangeably herein) is represented by a nucleotide sequence. A "polypeptide" is represented by an amino acid sequence. A "nucleic acid construct" is defined as a nucleic acid molecule which is isolated from a naturally occurring gene or which has been modified to contain segments of nucleic acids which are combined or juxtaposed in a manner which would not otherwise exist in nature. A nucleic acid molecule is represented by a nucleotide sequence. Optionally, a nucleotide sequence present in a nucleic acid construct is operably linked to one or more control sequences, which direct the production or expression of said peptide or polypeptide in a cell or in a subject.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject. "Operably linked" may also be used for defining a configuration in which a sequence is appropriately placed at a position relative to another sequence coding for a functional domain such that a chimeric polypeptide is encoded in a cell and/or in a subject.

"Expression" is construed as to include any step involved in the production of the peptide or polypeptide including, but not limited to, transcription, post-transcriptional modification, translation, post-translational modification and secretion.

A "control sequence" is defined herein to include all components which are necessary or advantageous for the expression of a polypeptide. At a minimum, the control sequences include a promoter and transcriptional and translational stop signals. Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the present invention, the term usually refers to an extrachromosomal, self-replicating vector which harbors a selectable antibiotic resistance.

An "expression vector" may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

A "polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

The sequence information as provided herein should not be so narrowly construed as to require inclusion of erroneously identified bases. The skilled person is capable of identifying such erroneously identified bases and knows how to correct for such errors.

Sequence identity herein of a polynucleotide, polynucleotide construct or of a polypeptide is preferably at least 50%. Preferably at least 50% is defined as preferably at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, at least 92%, at least 93%, at least 94%, at least 95%, at least 96%, at least 97%, more preferably at least 98%, more preferably at least 99%, or most preferably 100% sequence identity. In case of 100% sequence identity, the polynucleotide or polypeptide has exactly the sequence of the depicted SEQ ID NO. Sequence identity is preferably determined over the entire length of the subject sequence.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 10% of the value.

All patent and literature references cited in the present specification are hereby incorporated by reference in their entirety.

Unless otherwise indicated each embodiment as described herein may be combined with another embodiment as described herein.

The following examples are offered for illustrative purposes only, and are not intended to limit the scope of the present invention in any way.

Further Embodiments

Further embodiments of the invention are listed here below.

1. A modified bacteriophage capable of infecting a host bacterium, wherein the bacteriophage comprises a gene that is foreign to the bacteriophage and wherein said gene encodes a bacteriocin.
2. A modified bacteriophage according to embodiment 1, wherein the bacteriocin is a bacteriocin specific for Gram-negative bacteria, such as a microcin, a colicin-like bacteriocin or a tailocin.
3. A modified bacteriophage according to embodiment 1, wherein the bacteriocin is a bacteriocin specific for Gram-positive bacteria, such as class III bacteriocins.

4. A modified bacteriophage according to any one of the preceding embodiments, wherein the bacteriocin targets species of the host bacterium.

5. A modified bacteriophage according to any one of the preceding embodiments, wherein the bacteriocin does not target species of the host bacterium.

6. A modified bacteriophage according to any one of the preceding claims, wherein the bacteriocin has a protein sequence that can be classified into an InterPro homologous superfamily, family, or domain selected from the group consisting of: IPR036725, IPR037146, IPR038283, IPR036302, IPR024575, IPR028056, IPR000293, IPR009105, IPR024566, and IPR016128.

7. A modified bacteriophage according to any one of the preceding embodiments, wherein the bacteriocin is selected from the group consisting of Colicin M, Colicin E7, Colicin K, Colicin 5, Colicin E6 and Klebicin M, or wherein the bacteriocin has preferably at least 50% sequence identity with a bacteriocin selected from the group consisting of Colicin M (SEQ ID NO: 18), Colicin E7 (SEQ ID NO: 20), Colicin K (SEQ ID NO: 19), Colicin 5 (SEQ ID NO: 17), Colicin E6 (SEQ ID NO: 16) and Klebicin M (SEQ ID NO: 21) and/or is a variant bacteriocin that has different properties compared to the corresponding wild-type bacteriocin and has altered host specificity or altered specific activity.

8. A modified bacteriophage according to any of the preceding embodiments, wherein the host bacterium is selected from the group consisting of: *Acetinobacter, Chroinobacter, Bortadella, Burkholderia, Campylobacter, Staphylococcus, Pneumococcus, Enterococcus, Klebsiella, Escherichia, Pseudomonas, Salmonella, Shigella, Vibrio, Neisseria, Brucella, Haemophilus, Mycobacterium, Listeria, Legionella, Yersinia, Chlamydia, Clostridium, Helicobacter, Corynebacterium, Lactobacillus, Fusobacterium*, and *Streptococcus*.

9. A modified bacteriophage according to any one of the preceding embodiments, wherein the host bacterium is an *E. coli* species and wherein the bacteriocin targets said *E. coli* species.

10. A modified bacteriophage according to any one of the preceding embodiments, wherein the host bacterium is an *E. coli* species and wherein the bacteriocin does not target said *E. coli* species.

11. A modified bacteriophage according to any one of the preceding embodiments, wherein the host bacterium is an *Enterococcus* species, such as *Enterococcus faecalis*, and wherein the bacteriocin targets said *Enterococcus* species.

12. A modified bacteriophage according to any one of the preceding embodiments, wherein the host bacterium is an *Enterococcus* species, such as *Enterococcus faecalis*, and wherein the bacteriocin does not target said *Enterococcus* species.

13. A modified bacteriophage according to any one of the preceding embodiments, wherein the host bacterium is a *Klebsiella* species, such as *Klebsiella pneumoniae*, and wherein the bacteriocin targets said *Klebsiella* species.

14. A modified bacteriophage according to any one of the preceding embodiments, wherein the host bacterium is a *Klebsiella* species, such as *Klebsiella pneumoniae*, and wherein the bacteriocin does not target said *Klebsiella* species.

15. A modified bacteriophage according to any one of the preceding embodiments, wherein the bacteriophage is derived from wild-type bacteriophage *Klebsiella* phage K1, *E. coli* phage CM001, *E. coli* phage E2, *Enterococcus* phage Efs3, *Enterococcus* phage Efs7 or from *E. coli* phage phi41S.

16. A composition comprising a carrier and a modified bacteriophage as defined in any one of embodiments 1 to 15.

17. A composition according to embodiment 17, wherein the composition is a pharmaceutical composition.

18. A composition according to embodiment 16 or 17, wherein the composition is formulated for topical, intravenous, intramuscular, intrathecal, oral, intraperitoneal, vaginal, rectal, lumbar, or meningeal administration.

19. Use of a modified bacteriophage according to any one of embodiments 1 to 15 or of a composition according to any one of embodiments 16 to 18 for in vitro or ex vivo antibacterial decontamination.

20. A modified bacteriophage according to any one of embodiments 1 to 15 or of a composition according to any one of embodiments 16 to 18 for use as a medicament for the treatment of a bacterial infection in a subject in need thereof.

21. Use of a modified bacteriophage according to any one of embodiments 1 to 15 or of a composition according to any one of embodiments 16 to 18, for the production of a medicament for the treatment of a bacterial infection in a subject in need thereof.

22. A method of treatment of a bacterial infection in a subject in need thereof, comprising administration of a therapeutically effective amount of a modified bacteriophage according to any one of embodiments 1 to 15 or of a composition according to any one of embodiments 16 to 18 to the subject, thereby treating the bacterial infection.

23. A method of altering the microbial composition of a microbiome, comprising introducing a modified bacteriophage according to any one of embodiments 1 to 15 or of a composition according to any one of embodiments 16 to 18 into the microbiome.

24. Use of a modified bacteriophage according to any one of embodiments 1 to 15 or of a composition according to any one of embodiments 16 to 18 for in vitro or ex vivo detection of a bacterial pathogen.

EXAMPLES

Example 1: Phages Carrying Active Bacteriocin Payloads

Introduction

Figure 1:
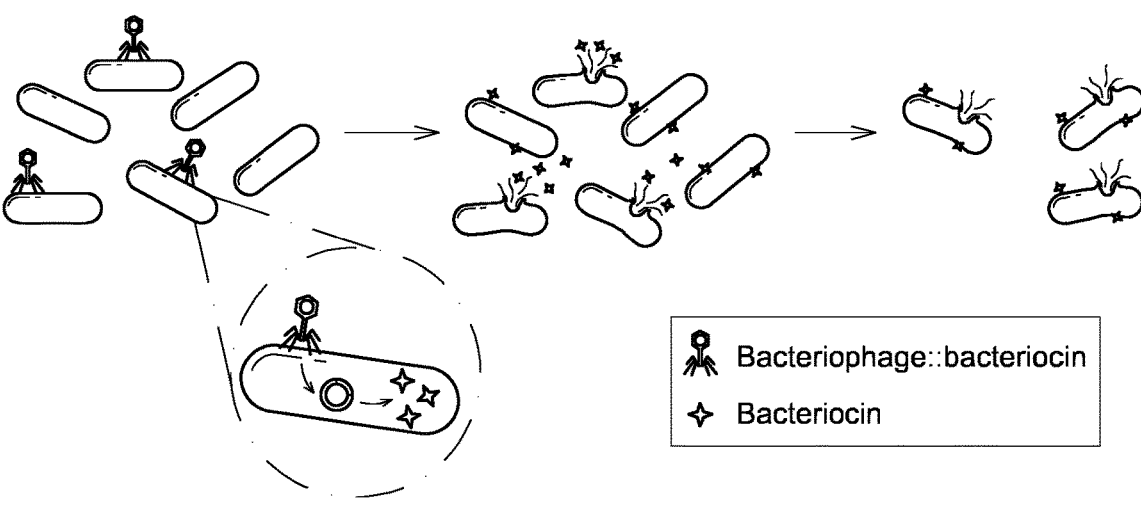
FIG. 1. Graphical representation

The antibiotic resistance crisis and adverse effects caused by antibiotic-induced microbiome dysbiosis highlight the need for novel and more pathogen-specific antibacterial interventions. The therapeutic use of bacteriophages/phages (i.e., viruses that infect bacteria) is one promising alternative option. While phages offer the required pathogen-specificity, it remains difficult to completely inactivate all cells from a population of target cells. This is due to the evolution of effective phage resistance mechanisms such as receptor diversification, adaptive CRISPR-Cas immunity, restriction/modification, or abortive infection that bacteria use to counteract phage predation. To circumvent this limitation, multiple phages with distinct infection pathways are typically combined to replace or complement antibiotic therapy. Here, we demonstrate how individual phages can be engineered to encode bacteriocins as genetic payloads; a graphical representation is depicted in FIG. 1. Heterologous bacteriocins, i.e. bacteriocins that are foreign to the bacteriophage, are expressed during infection and released upon host cell lysis to locally improve and expand the antibacterial effect of their wild type parental phage. Bacteriocins may act on the same strain or species to target resistant sub-populations and other survivors of phage infection. Alternatively, bacteriocins may be produced by one species in a poly-microbial infection and released to target a second pathogen. To demonstrate these concepts, we engineered virulent phages targeting *E. coli, Klebsiella,* and *Enterococcus* to produce the bacteriocins Colicin M, Colicin E7, or KlebicinM. These phages control their target pathogens with higher efficacy, prevent to amplification of resistant sub-populations during prolonged treatment, and enable cross-genus targeting to control polymicrobial populations.

Results and Discussion

Colicin- and Klebicin-Encoding Phages Produce Active Bacteriocin Payloads During Infection Bacteriophages that infect *Klebsiella* (phage K1), *E. coli* (phage CM001), or *Enterococcus* (phages Efs3 and Efs7) were engineered to encode bacteriocin genes within the late gene cluster where their expression is driven from strong late viral promoters. The genome sequences are presented in the sequence listing part of this application; an overview of the sequences is given in Table 1. Ribosomal binding sites were inserted immediately upstream of each bacteriocin gene to ensure efficient translation initiation. To test phage-mediated bacteriocin expression, bacterial host cells were infected using the soft-agar overlay method to produce unpurified high-titer lysates containing progeny phage and any expressed viral and bacterial gene (including bacteriocin). Lysates were sterile-filtered and tested for antibacterial effect by spotting on bacterial lawns (FIG. 2). The antibacterial effects were judged visually (−,+,++,+++) as shown in FIG. 2A and compared on a selection of 26 clinical *E. coli* and 24 clinical *Klebsiella* isolates (FIG. 2B). It was demonstrated that our modified, recombinant, phages produce active bacteriocin payloads with varying activity range on urological isolates. So far, Colicin E7 (co/E7) and Klebicin M (kvarM) were identified as the bacteriocins with excellent activity profiles. Testing of more bacteriocins in various phages is ongoing, such as Colicin E7 in *E. coli* phage E2, which also demonstrates a good activity profile.

Bacteriocin Production Enhances Killing of Phage Susceptible Target Populations

In prolonged liquid infection assays, most phages cannot efficiently control their bacterial host resulting in bacterial outgrowth. This is due to the presence of phage-resistant subpopulations, whose resistance phenotype can be genetic or transient. Bacteriocin-producing phages may enable killing of such resistant sub-populations and therefore enhance the antibacterial effect of their wild-type counterparts (FIG. 3A). Here, we compared host killing of wild-type and engineered phages using 12-18 h liquid infection assays in LB or synthetic human urine medium (SHU) (FIGS. 3B/C). Bacterial growth or killing was visualized by reading the optical density at 600 nm. Both the Klebicin M-producing *Klebsiella* phage K1 (K1:kvarM) and the Colicin E7-producing *E. coli* phage CM001 (CM001::colE7) resulted in killing and long-term suppression of bacterial growth, whereas the wild-type parental phages could only control bacterial growth for 8-10 hours. This data demonstrates the superior killing of phage susceptible-host populations by bacteriocin-producing bacteriophages; complete sterilization can be achieved.

Bacteriocin Production Enables Cross-Genus Targeting

Many bacterial infections can be caused by or be associated with the presence of multiple bacterial genera. For example, such polymicrobial infections are frequently observed within the urinary tract. The main contributors to urinary tract infections (UTIs) are *E. coli, Klebsiella,* and *Enterococcus faecalis.* To mimic the application of engineered, bacteriocin-producing phages for the control of polymicrobial UTIs, we co-cultivated *E. faecalis* either with a urological *Klebsiella* isolate (FIGS. 4A/B) or with a urological *E. coli* isolate (FIGS. 5A/B). These co-cultures were subsequently infected with wild-type *Enterococcus* phages or with engineered phage-derivatives that produce Klebicin M or Colicin E7 within the infected *Enterococcus* cell, respectively. Upon host-cell lysis, the released bacteriocins were able to successfully control the polymicrobial infection, whereas the wild-type phages could not. This data demonstrates that bacteriocin-producing phages can be used for cross-genus targeting of polymicrobial infections.

Example 2: Enhancing Bacteriophage Therapeutics Through In Situ Production and Release of Heterologous Antimicrobial Effectors Bacteriophages operate via pathogen-specific mechanisms of action distinct from conventional, broad-spectrum antibiotics and are emerging as promising alternatives. However, phage-mediated killing is often limited by bacterial resistance development (1, 2). Here, we engineer phages for target-specific effector gene delivery and host-dependent production of colicin-like bacteriocins and cell wall hydrolases. Using urinary tract infection (UTI) as a model, we show how heterologous effector phage therapeutics (HEPTs) suppress resistance and improve uropathogen killing by dual phage- and effector-mediated targeting. Moreover, we designed HEPTs to control polymicrobial uropathogen communities through production of effectors with cross-genus activity. Using a phage-based companion diagnostic (3), we identified potential HEPT responder patients and treated their urine ex vivo. Compared to wildtype phage, a colicin E7-producing HEPT demonstrated superior control of patient *E. coli* bacteriuria. Arming phages with heterologous effectors paves the way for successful UTI treatment and represents a versatile tool to enhance and adapt phage-based precision antimicrobials.

Main

Currently, conventional, small-molecule antibiotics with broad target specificity are the most effective treatments against bacterial infections. However, the global emergence and spread of antimicrobial resistance (AMR) (4), as well as adverse effects caused by antibiotic-induced microbiome dysbiosis, highlight the need for novel and more pathogen-specific antimicrobial interventions (5,6). Bacteriophages (phages), bacteriocins, synthetic antimicrobial peptides, and target-specific cell wall hydrolases (e.g., phage-derived endolysins) are currently being developed as precision antimicrobials (7). Among these, phages are highly promising because of their ubiquity, pathogen specificity, and ability to self-replicate (8,9). Although the killing of host bacteria by phages is largely independent of the host drug-resistance profile, treatment with phages often fails to inactivate all bacterial cells within a target population. This can be due to phage tolerance (10) or resistance mechanisms that bacteria employ to counteract viral predation, including the production of extracellular matrices, mutation or reduced expression of phage receptors, adaptive CRISPR-Cas immunity, restriction/modification systems, abortive infection systems, and a growing number of other resistance mechanisms described in the literature (11, 12).

Recent advances in CRISPR-Cas technology and synthetic biology have enabled the rapid modification of phage genomes beyond model phages (such as T4, T7, or lambda) to include therapeutic phage candidates that are typically less well-studied (13). As a result, engineering has been applied to (i) adapt phage tropism through directed receptor binding protein modification (14-17), (ii) construct sequence-specific antimicrobials through phage-mediated, pathogen-specific delivery of programmed CRISPR-Cas modules (18,19), (iii) deliver toxic proteins as genetic payloads (20), (iv) develop rapid phage-based (companion) diagnostics through the delivery of reporter genes (reporter phages) (13,21), and (v) optimize therapeutic phages for experimental therapy (22).

In this study, we demonstrate how diverse phages can be engineered to encode bacteriocins and cell wall hydrolases as antimicrobial effector genes, a concept we coin heterologous effector phage therapeutics (HEPTs). Here, effector genes are expressed during infection and their products released upon host cell lysis to function as secondary pathogen-specific antimicrobials, thereby complementing and enhancing phage-mediated killing. As a model system, we focused on developing HEPTs as precision antimicrobials against UTI pathogens (concept: FIG. 6A). UTIs are among the most common community-acquired and healthcare-associated microbial infections in all age groups and a major public health concern, resulting in annual healthcare costs exceeding 1.6 billion dollars in the US alone (23). While the most prevalent causative agent of UTIs is *Escherichia coli*, the microbial etiology is complex and can involve a wide range of Gram-negative or Gram-positive bacteria and certain fungi (24). An analysis of 340 isolates acquired from 231 incidents of UTI during 2020 in Zurich, Switzerland (the Zurich Uropathogen Collection; FIG. 9) identified 26 different bacterial species, with *E. coli* (34%), *Enterococcus faecalis* (17%), and *Klebsiella pneumoniae* (14%) as the most prevalent uropathogens, which is consistent with previous etiological studies on UTIs (24).

Guided by these observations, we engineered HEPTs using five distinct and strictly lytic phages that target the predominant uropathogens *E. coli* (phages E2 and CM001), *E. faecalis* (phages EfS3 and EfS7), and *K. pneumoniae* (phage K1). These phages represent various phylogenetic families with distinct virion morphologies and genome sizes (3,25) (FIG. 6B). To target Gram-negative uropathogens, we selected four colicin-like bacteriocins (CLBs) as effectors, which are active against either *E. coli* (colicins E6, M, and E7; green) or *K. pneumoniae* (klebicin M; purple). CLBs are protein toxins with narrow-spectrum activity, characterized by a distinct, three-domain architecture that mediates receptor binding (central domain), Ton- or Tol-dependent translocation (N-terminal domain), and periplasmic or intracellular toxicity (C-terminal domain) (26). The cytotoxicity of CLBs that were selected for HEPT engineering is mediated by periplasmic peptidoglycan biosynthesis inhibition (colicin M, klebicin M), intracellular 16s rRNase activity (colicin E6), or unspecific cytosolic nuclease activity (colicin E7) (26, 27). To target the Gram-positive uropathogen *E. faecalis*, we employed a phage-derived, chimeric cell wall-hydrolase (EC300; blue) that recognizes and degrades *E. faecalis* cell walls with high specificity (28). EC300 was engineered by fusing an M23 endopeptidase domain from a virion-associated lysin with a cell wall binding domain of an *E. faecalis* phage endolysin (28).

Figure 10A:
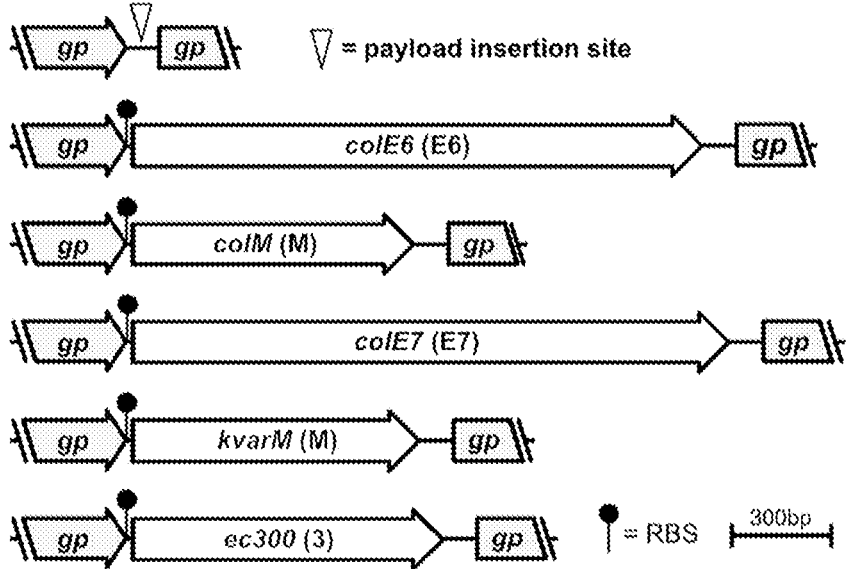
Figure 10B:
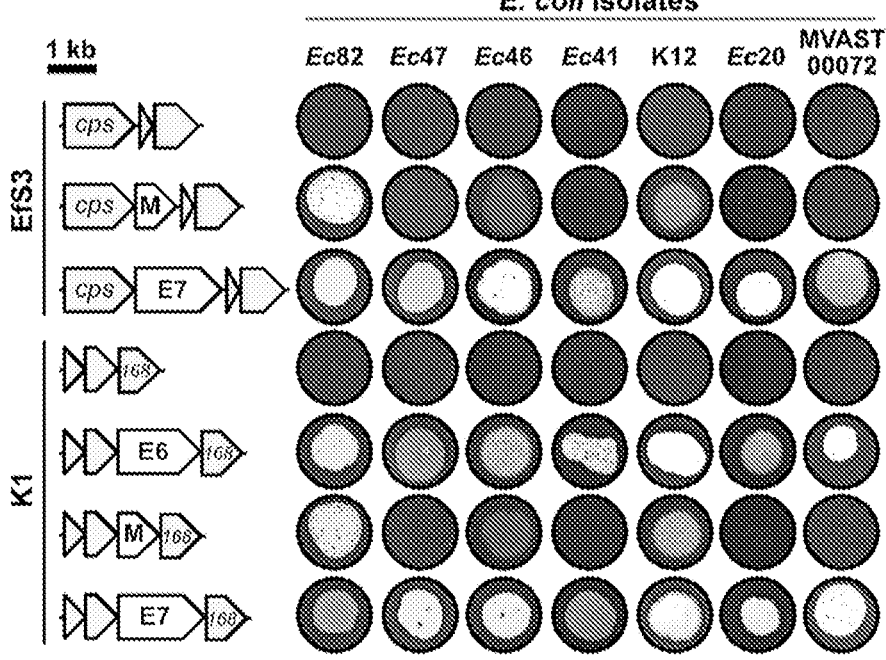
Figure 10C:
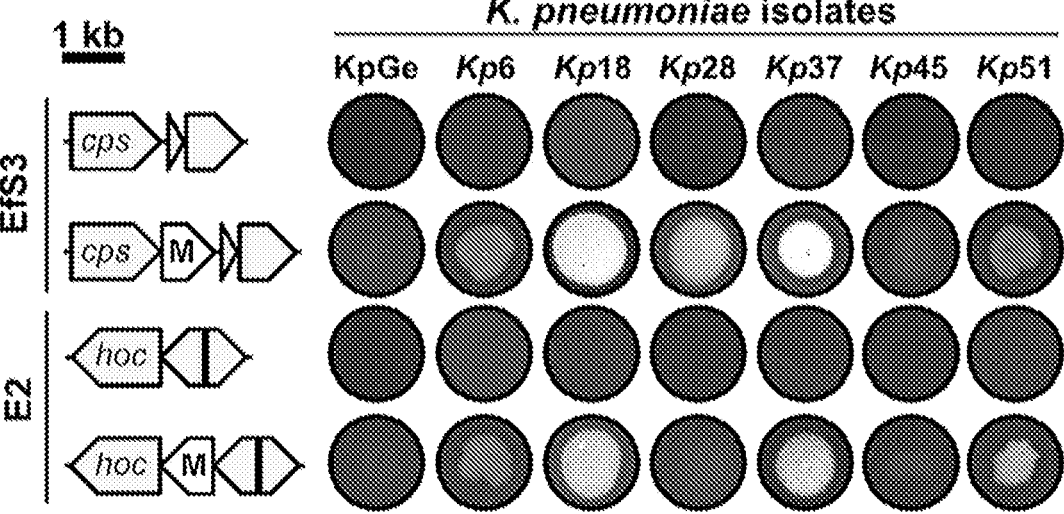
Figure 10D:
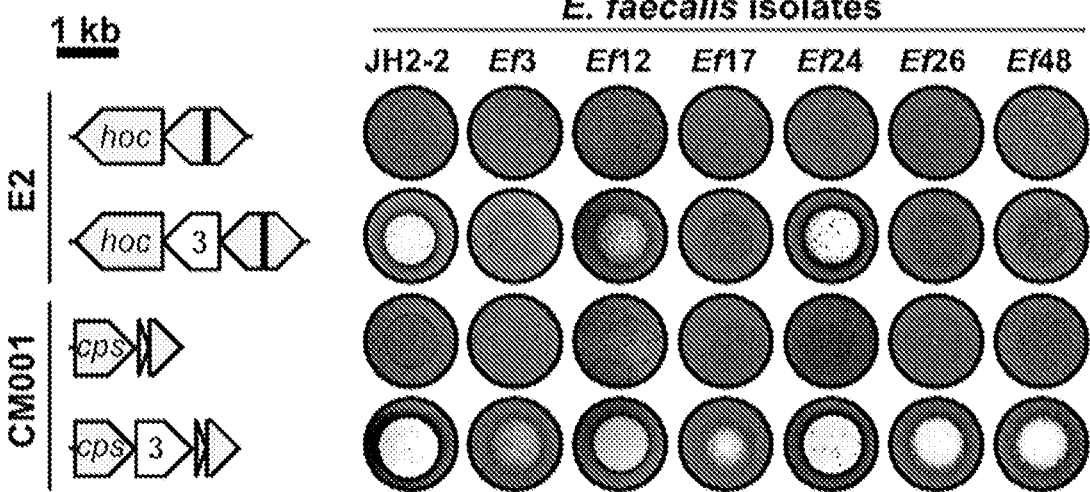

All effector genes were codon-optimized to match scaffold target species specificity (29) and integrated within the phage structural gene cassette alongside a strong ribosomal binding site to guide late promoter-driven expression (see FIG. 10A). Engineered HEPT candidates were constructed either using CRISPR-Cas9-assisted engineering (3, 15, 25) or by rebooting synthetic genomes in suitable surrogate hosts (30). To avoid toxicity, CLB-encoding HEPTs were engineered and amplified under constitutive expression of their respective immunity proteins. The production of active effector protein upon engineered phage infection was demonstrated by spot assays using crude wildtype (WT) phage or HEPT lysates on a selection of clinical target strains (FIG. 10B, C, D). To ensure that phage activity does not interfere with these assays, we tested lysates from engineered phages producing effectors with cross-genus activity. All effectors were produced and active against a broad range of urine-derived isolates of the respective target species with variable levels of activity depending on the phage scaffold. The klebicin M and EC300 encoding HEPTs targeted up to 54% and 92% of tested isolates, respectively. Among the three colicins, colicin E7 presented the broadest range of activity with HEPT EfS3::co/E7 active against 70% of the 56 *E. coli* isolates tested.

Polymicrobial infections are commonly observed within the urinary tract, particularly during catheter-associated UTIs (31), which may complicate therapeutic phage selection, combination, and treatment. Interestingly, analysis of the Zurich Uropathogen Collection revealed 34% of UTI cases (78/231) as polymicrobial with *E. faecalis* identified as a common co-infector associated with polymicrobial UTIs involving *E. coli* (46%) and *K. pneumoniae* (39%) (FIG. 6C). We therefore assessed the ability of HEPTs to deliver effectors with cross-genus activity to target polymicrobial communities composed of different combinations of clinical isolates through enzymatic collateral damage (cross-targeting HEPTs, FIG. 6 C-H). Using turbidity reduction and time kill assays combined with differential plating, we demonstrate the ability of HEPTs EfS3::co/E7 and EfS7::co/E7 to infect and kill *E. faecalis* cells (P, producer) while simultaneously eradicating co-cultured *E. coli* (R, recipient) within two hours of treatment through in situ release of colicin E7 effectors (FIG. 6 C, D). Similarly, we demonstrate that the klebicin M-producing HEPTs EfS3::kvarM and Efs7:: kvarM can successfully control co-cultures of *E. faecalis* (P) and *K. pneumoniae* (R) (FIG. 6 E, F), suggesting that CLB effectors provide a viable strategy for cross-genus targeting.

Since the protective peptidoglycan layer of Gram-positive pathogens such as *E. faecalis* is externally accessible, cell wall hydrolases are also promising enzyme antibiotics (enzybiotics) for cross-genus HEPT engineering. As shown in FIG. 6 G, H, we demonstrate the ability of an EC300-producing HEPT based on *E. coli* phage CM001 (CM001:: ec300) to target *E. faecalis* in co-culture, resulting in approximately 4-log reduction in *E. faecalis* after six hours of treatment for a co-culture of *E. coli* Ec20 (P) and *E. faecalis* Ef12 (R) (FIG. 6H). In clinical practice, polymicrobial UTIs would require application of multiple phages for treatment. Using a combination of two cross-genus HEPTs (E2::kvarM and K1::colE7), we were able to demonstrate a strongly enhanced killing of an *E. coli* and *K. pneumoniae* co-culture, providing a promising strategy to tackle polymicrobial UTIs (FIG. 11A). During polymicrobial UTIs, each bacterial species could be leveraged as an effector-producing host, even if it might not be the causative agent.

Regardless of the importance of polymicrobial infections, most UTIs are caused by a single uropathogen, with *E. coli* and *K. pneumoniae* as predominant agents (24). Infection of monocultures with WT phages typically leads to substantial initial host killing, as can be observed in turbidity reduction assays. However, within hours of infection, stable or transient phage resistance frequently occurs, leading to regrowth of phage resistant populations. To demonstrate this well-known limitation for phage treatment, we infected urine-derived *E. coli* (Ec20 and Ec41) or *K. pneumoniae* (Kp18, Kp28, and Kp37) isolates with WT phages E2 or K1, respectively. As expected, regrowth was observed within <18 h and a second round of infection demonstrated that these cells no longer responded to phage challenge, with both transient and stable phage resistance identified for individual clones isolated after the second round of infection (FIG. 12).

Figure 7A:
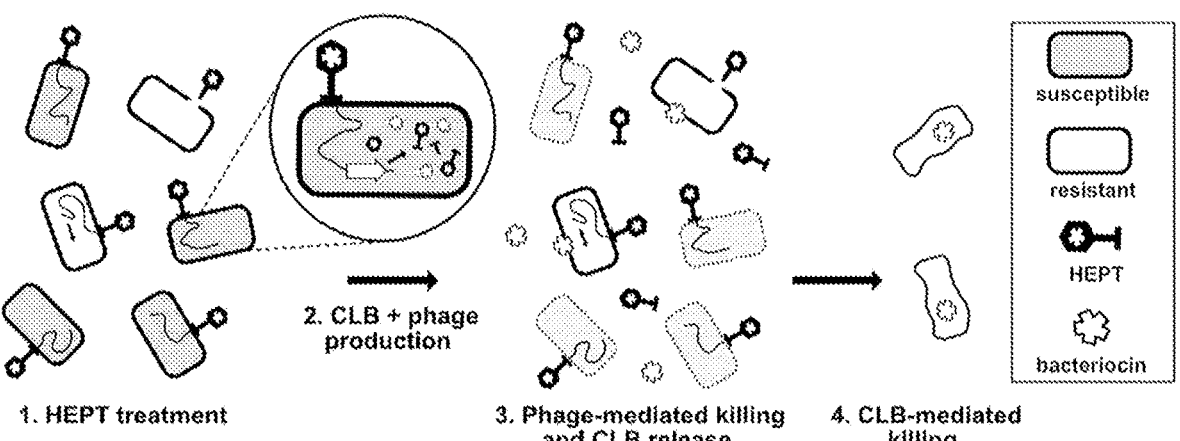
Figure 7B:
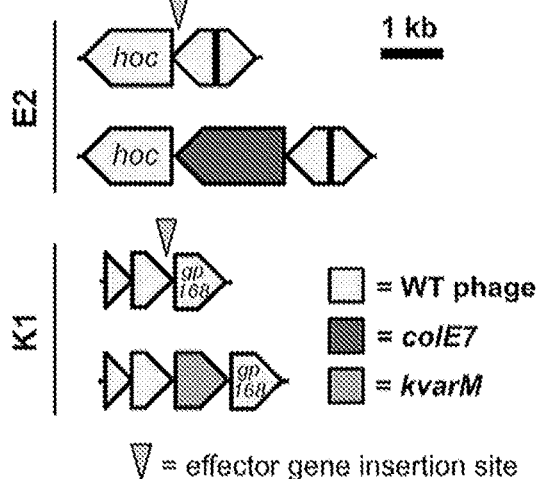
Figures 7C, 7D:
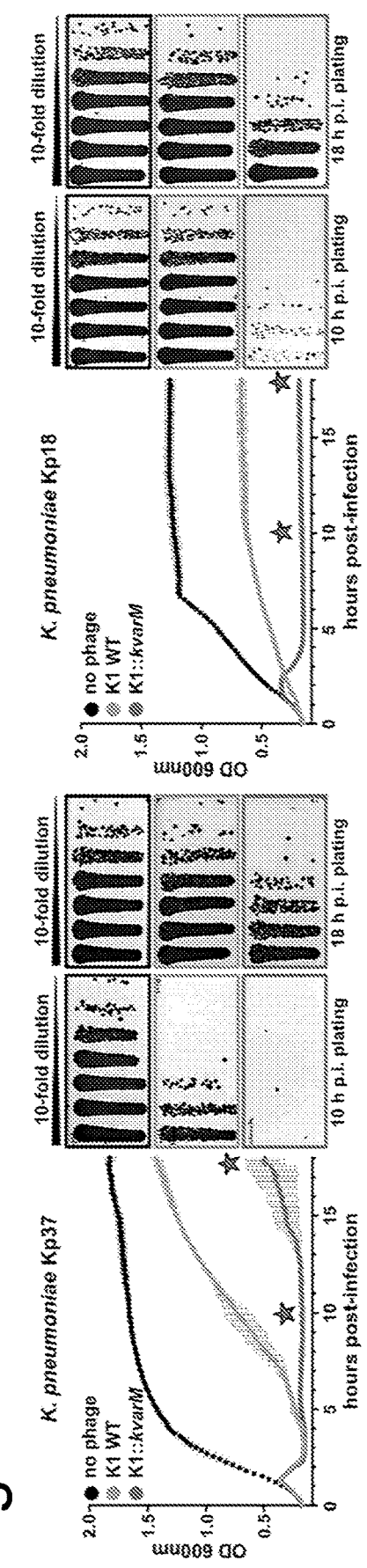

To circumvent this limitation, HEPTs were engineered to target resistant subpopulations through phage-mediated delivery of CLBs that provide an orthogonal killing mechanism against the same target species (self-targeting HEPTs, FIG. 7A). To this end, we constructed HEPTs E2::colE7 and K1::kvarM (FIG. 7B) to treat *E. coli* or *Klebsiella* monocultures and compared performance to their WT phage counterparts. Depending on the target isolate, E2 WT treatment led to rapid (*E. coli* Ec20) or delayed (*E. coli* Ec41) regrowth due to the expansion of resistant subpopulations. Strikingly, treatment with E2::colE7 led to a sustained (18 h) reduction in optical density and dramatic reduction of *E. coli* cell counts (>6-log reduction as compared to E2 WT) (FIG. 7C). Similar results were obtained for the self-targeting HEPT K1::kvarM, which strongly reduced *Klebsiella* cell counts at 10 h post-infection (p.i.) and delayed the regrowth of *Klebsiella* cells when measured at 18 h p.i. (FIG. 7D). Akin to the use of dual cross-targeting HEPTs (FIG. 11A), the combination of E2::co/E7 and K1::kvarM led to enhanced control of *E. coli* and *Klebsiella* co-cultures compared to combinations containing WT phages (FIG. 11B). Overall, through in situ production of self-targeting effectors, HEPTs provide an effective two-pronged attack to target bacteria and prevent or delay their regrowth.

In the future, phage-based precision antimicrobials will most likely be designed and implemented as personalized treatment options. Therefore, a rapid and reliable companion diagnostic would be helpful to guide phage selection and/or predict therapeutic success. To assess the performance of self-targeting HEPTs against *E. coli* in patient urine, we combined our recently developed reporter phage-based diagnostic (3) with ex vivo urine treatment using HEPT E2::colE7 (workflow: FIG. 8A). To this end, 39 patient urine samples were collected and subjected to reporter phage-based pathogen identification and phage susceptibility screening using a nanoluciferase-encoding phage E2 (E2::nluc) (3). Reporter phage-induced bioluminescence was quantified within 4.5 h as an indicator of successful phage genome delivery and expression. Concurrently, the presence of *E. coli* in individual urine specimens was screened and confirmed using differential plating. Eight urine samples were positive for *E. coli*, seven of which were detected by E2::nluc (FIG. 8B, urinalysis). To assess the advantage of heterologous effector delivery, fresh urine samples were subjected to HEPT (E2::colE7) or WT phage treatment, with *E. coli* killing assessed over 24 h using time kill assays (FIG. 8C, ex vivo). In addition, patient-derived *E. coli* strains were isolated and tested for phage and colicin E7 susceptibility, with phage susceptibility defined as the ability to form plaques (FIG. 8B, FIG. 13). Specimen #5 was excluded due to the presence of >$10^7$ CFU/mL *K. pneumoniae* (polymicrobial infection). The remaining six patient isolates could be classified into three categories based on their susceptibility profiles: (I) phage and colicin sensitive, (II) phage resistant but colicin sensitive, and (III) phage sensitive but colicin resistant. Compared to E2 WT, improved *E. coli* killing by E2::colE7 was observed for both ex vivo treatments of urine in category I (specimens #7 and #30), which was subsequently confirmed in vitro using turbidity reduction assays (FIG. 8C, in vitro). In category II (specimens #12 and #16), a slight enhancement of activity was observed during ex vivo HEPT treatment; however, no improvement could be validated during in vitro turbidity reduction analysis. This was attributed to incomplete infectivity of phage E2 towards specimens #12 and #16, as observed by a lack of plaque formation. As expected, due to a lack of colicin sensitivity for specimens #21 and #32, no difference in activity was observed between E2 WT and E2::colE7 within category III. Overall, the ex vivo study demonstrated enhanced HEPT-mediated killing of *E. coli* in fresh patient urine, provided that the isolate is susceptible to both phage and effector, e.g., colicin E7. For future implementation of HEPTs and other phage-based therapeutics, careful and rapid screening of relevant susceptibility profiles, e.g., using reporter phage companion diagnostics, will be an essential component to guide their therapeutic use.

In conclusion, we present HEPTs as precision antimicrobials that combine the inherent, pathogen-specific killing activity of bacteriophages with in situ production and release of secondary antimicrobial effectors. This two-pronged approach enhances the antimicrobial activity of phages, is capable of suppressing outgrowth of phage resistant subpopulations, and can be harnessed to provide cross-genus control of bacterial pathogens using a single HEPT. Through the careful selection of phage scaffolds and heterologous effectors, HEPTs provide a customizable platform for targeted antimicrobial therapy.

REFERENCES

1. Gurney, J., Brown, S. P., Kaltz, O. and Hochberg, M. E. (2020) Steering Phages to Combat Bacterial Pathogens. *Trends Microbiol,* 28, 85-94.
2. Oechslin, F. (2018) Resistance Development to Bacteriophages Occurring during Bacteriophage Therapy. *Viruses,* 10.
3. Du, J., Meile, S., Staubli, S., Koliwer-Brandl, H., Piffaretti, P., Leitner, L., Matter, C. I., Baggenstos, J., Milek, S., Gübeli, C. et al. (2022) Engineered reporter phages for rapid detection of *Escherichia coli* and *Klebsiella* spp. in urine. *Cell Rep Med,* submitted.
4. Antimicrobial Resistance, C. (2022) Global burden of bacterial antimicrobial resistance in 2019: a systematic analysis. *Lancet,* 399, 629-655.
5. (2019) Antibiotic resistance threats in the united states. *U.S. Department of Health and Human Services,* CDC.
6. de la Fuente-Nunez, C., Torres, M. D., Mojica, F. J. and Lu, T. K. (2017) Next-generation precision antimicrobials: towards personalized treatment of infectious diseases. *Curr Opin Microbiol,* 37, 95-102.
7. Mills, S., Ross, R. P. and Hill, C. (2017) Bacteriocins and bacteriophage; a narrow-minded approach to food and gut microbiology. *FEMS Microbiol Rev,* 41, S129-S153.
8. Gordillo Altamirano, F. L. and Barr, J. J. (2019) Phage Therapy in the Postantibiotic Era. *Clin Microbiol Rev,* 32.

9. Meile, S., Du, J., Dunne, M., Kilcher, S. and Loessner, M. J. (2022) Engineering therapeutic phages for enhanced antibacterial efficacy. *Curr Opin Virol,* 52, 182-191.

10. Tzipilevich, E., Pollak-Fiyaksel, O., Shraiteh, B. and Ben-Yehuda, S. (2022) Bacteria elicit a phage tolerance response subsequent to infection of their neighbors. *EMBO J,* 41, e109247.

11. Bernheim, A. and Sorek, R. (2020) The pan-immune system of bacteria: antiviral defence as a community resource. *Nat Rev Microbiol,* 18, 113-119.

12. Labrie, S. J., Samson, J. E. and Moineau, S. (2010) Bacteriophage resistance mechanisms. *Nat Rev Microbiol,* 8, 317-327.

13. Kilcher, S. and Loessner, M. J. (2019) Engineering Bacteriophages as Versatile Biologics. *Trends Microbiol,* 27, 355-367.

14. Dunne, M., Rupf, B., Tala, M., Qabrati, X., Ernst, P., Shen, Y., Sumrall, E., Heeb, L., Pluckthun, A., Loessner, M. J. et al. (2019) Reprogramming Bacteriophage Host Range through Structure-Guided Design of Chimeric Receptor Binding Proteins. *Cell Rep,* 29, 1336-1350 e1334.

15. Yehl, K., Lemire, S., Yang, A. C., Ando, H., Mimee, M., Torres, M. T., de la Fuente-Nunez, C. and Lu, T. K. (2019) Engineering Phage Host-Range and Suppressing Bacterial Resistance through Phage Tail Fiber Mutagenesis. *Cell,* 179, 459-469 e459.

16. Ando, H., Lemire, S., Pires, D. P. and Lu, T. K. (2015) Engineering Modular Viral Scaffolds for Targeted Bacterial Population Editing. *Cell Syst,* 1, 187-196.

17. Yosef, I., Goren, M. G., Globus, R., Molshanski-Mor, S. and Qimron, U. (2017) Extending the Host Range of Bacteriophage Particles for DNA Transduction. *Mol Cell,* 66, 721-728 e723.

18. Bikard, D., Euler, C. W., Jiang, W., Nussenzweig, P. M., Goldberg, G. W., Duportet, X., Fischetti, V. A. and Marraffini, L. A. (2014) Exploiting CRISPR-Cas nucleases to produce sequence-specific antimicrobials. *Nat Biotechnol,* 32, 1146-1150.

19. Citorik, R. J., Mimee, M. and Lu, T. K. (2014) Sequence-specific antimicrobials using efficiently delivered RNA-guided nucleases. *Nat Biotechnol,* 32, 1141-1145.

20. Cass, J., Barnard, A. and Fairhead, H. (2021) Engineered Bacteriophage as a Delivery Vehicle for Antibacterial Protein, SASP. *Pharmaceuticals (Basel),* 14.

21. Meile, S., Kilcher, S., Loessner, M. J. and Dunne, M. (2020) Reporter Phage-Based Detection of Bacterial Pathogens: Design Guidelines and Recent Developments. *Viruses,* 12.

22. Dedrick, R. M., Guerrero-Bustamante, C. A., Garlena, R. A., Russell, D. A., Ford, K., Harris, K., Gilmour, K. C., Soothill, J., Jacobs-Sera, D., Schooley, R. T. et al. (2019) Engineered bacteriophages for treatment of a patient with a disseminated drug-resistant *Mycobacterium abscessus. Nat Med,* 25, 730-733.

23. Foxman, B., Barlow, R., D'Arcy, H., Gillespie, B. and Sobel, J. D. (2000) Urinary tract infection: self-reported incidence and associated costs. *Ann Epidemiol,* 10, 509-515.

24. Flores-Mireles, A. L., Walker, J. N., Caparon, M. and Hultgren, S. J. (2015) Urinary tract infections: epidemiology, mechanisms of infection and treatment options. *Nat Rev Microbiol,* 13, 269-284.

25. Meile, S., Du, J., Grossman, S., Koliwer-Brandl, H., Piffaretti, P., Leitner, L., Baggenstos, J., Matter, C. I., Milek, S., Gübeli, C. et al. (2022) Engineered reporter phages for rapid detection of *Enterococcus faecalis* in urine. *Cell Rep Med,* submitted.

26. Cascales, E., Buchanan, S. K., Duche, D., Kleanthous, C., Lloubes, R., Postle, K., Riley, M., Slatin, S. and Cavard, D. (2007) Colicin biology. *Microbiol Mol Biol Rev,* 71, 158-229.

27. Cherier, D., Patin, D., Blanot, D., Touze, T. and Barreteau, H. (2021) The Biology of Colicin M and Its Orthologs. *Antibiotics (Basel),* 10.

28. Proenca, D., Leandro, C., Garcia, M., Pimentel, M. and Sao-Jose, C. (2015) EC300: a phage-based, bacteriolysin-like protein with enhanced antibacterial activity against *Enterococcus faecalis. Appl Microbiol Biotechnol,* 99, 5137-5149.

29. Grote, A., Hiller, K., Scheer, M., Munch, R., Nortemann, B., Hempel, D. C. and Jahn, D. (2005) JCat: a novel tool to adapt codon usage of a target gene to its potential expression host. *Nucleic Acids Res,* 33, W526-531.

30. Kilcher, S., Studer, P., Muessner, C., Klumpp, J. and Loessner, M. J. (2018) Cross-genus rebooting of custom-made, synthetic bacteriophage genomes in L-form bacteria. *Proc Natl Acad Sci USA,* 115, 567-572.

31. Kline, K. A. and Lewis, A. L. (2016) Gram-Positive Uropathogens, Polymicrobial Urinary Tract Infection, and the Emerging Microbiota of the Urinary Tract. *Microbiol Spectr,* 4.

32. World Medical, A. (2001) World Medical Association Declaration of Helsinki. Ethical principles for medical research involving human subjects. *Bull World Health Organ,* 79, 373-374.

Supplemental Material to Example 2

Materials and Methods

Bacterial Strains and Culture Conditions

*E. coli* BL21 (New England Biolabs), *E. coli* Ec20 (1), *K. pneumoniae* KpGe (2), *E. faecalis* JH2-2, and *E. faecalis* Ef57 (3) were used as phage propagation and engineering hosts. *E. coli* XL1-Blue MRF' (Stratagene) was used as a cloning host for plasmid construction. Clinical strains used in this study include isolates taken from the Zurich Uropathogen Collection; a library of 665 patient isolates identified from urine specimens of patients from the Department of Neuro-Urology, Balgrist University Hospital, Zurich, Switzerland acquired between January and December 2020 and provided after routine testing by the Institute of Medical Microbiology (IMM), University of Zurich. Gram-negative bacteria were grown at 37° C. in Lysogeny Broth (LB) or Synthetic Human Urine (SHU (4)). Gram-positive bacteria were cultivated at 37° C. in BHI-fc broth (37 g/L Brain-Heart-Infusion broth from Biolife Italiana, 4 g/L Phages were propagated on their respective propagation hosts using the soft-agar-overlay method as described previously (1,3). To avoid toxicity, co/E7-encoding HEPTs E2::colE7, K1::colE7, and K1::colE6 were propagated in the presence of their immunity plasmids, plm_E7 and plm_E6, respectively. In brief, after overnight incubation, phage particles were extracted using 5 ml SM buffer per plate (50 mM Tris, pH 7.4, 100 mM NaCl, 8 mM $MgSO_4$) and filter-sterilized (0.2 µm) to obtain crude phage lysates (used for effector susceptibility testing as described below). Phage lysates were further purified and concentrated by PEG precipitation (7% PEG 8000 and 1M NaCl) followed by cesium chloride isopycnic centrifugation and finally dialyzed against a 1000-fold excess of SM buffer.

Phage Genome Sequencing

*E. coli* phage CM001 was isolated from a mixture of wastewaters collected in Switzerland using *E. coli* Ec20 as a host, purified using three sequential rounds of the soft-agar-overlay method, and further propagated as described above. Genomic DNA was extracted from purified phage particles using the phenol:chloroform:isoamyl alcohol (25:24:1) extraction method. Purified DNA was Illumina sequenced (2×150 bp) by Eurofins Genomics Europe Sequencing GmbH (Constance, Germany). A single contig was obtained by de novo assembly using the CLC Genomics Workbench version 20 (QIAGEN Bioinformatics) with default settings. Coding DNA sequence (CDS) identification and annotation was performed using the RAST server (5), with tRNAscan-SE used to identify possible tRNA genes (none detected) (6). Subsequent manual curation and validation was performed using related *E. coli* phage K1H (NC_027994) as a reference genome. The final annotated genome of phage CM001 is available from the GenBank database (UTI-CM001, OM810255) alongside previously sequenced genomes of phage E2 (OL870316), K1 (OL870318), EfS3 (OL870611), and EfS7 (OL870612).

Transmission Electron Microscopy

Phage particles were negatively stained for 20 seconds with 2% uranyl acetate on carbon-coated copper grids (Quantifoil) and observed at 100 kV on a Hitachi HT 7700 equipped with an AMT XR81 B Peltier cooled CCD camera (8M pixel) at the ScopeM facility, ETH Zurich.

CRISPR-Cas9-Assisted Phage Engineering

All HEPTs based on phages E2, K1, EfS3, and EfS7:: colM/kvarM were constructed using the homologous recombination-based and CRISPR-Cas9-assisted engineering as previously described (1,3). In short, WT phages were propagated in the presence of the respective editing template (pEdit) to enable sequence-specific transgene integration through homologous recombination. WT phages were selectively restricted using a SpyCas9-based counterselection system (pSelect) directed at the flanking homology arms within individual phage genomes. Silent mutations within the protospacer-adjacent motifs (PAMs) on the homology arms of pEdit enable CRISPR-escape and enrichment of engineered phage. When PAM mutation is impossible, multiple silent mutations were introduced within the SpyCas9-targeted seed sequence (12 nucleotides immediately upstream of the PAM) to abrogate CRISPR targeting.

Phage Genome Assembly and Rebooting

EfS7::co/E7 and CM001::ec300 genomes were assembled in vitro from overlapping (~40 bp) PCR fragments using the Gibson isothermal method (NEBuilder HiFi DNA assembly master mix, NEB). 20 ng of PCR products per 1 kb of genomic fragment length were used for assembly. Synthetic genomes of *E. faecalis* HEPTs were rebooted through transfection into *L. monocytogenes* Rev2L L-form bacteria as previously described (7). To reboot CM001::ec300, 3 µl of assembly mixture was electroporated into 42 µL of electrocompetent *E. coli* XL1-Blue cells at 1.8 kV, 25 µF, 200Ω using a BTX ECM630 electroporator (BTX Molecular Delivery Systems, MA, USA). 1 mL of SOC medium was supplemented immediately after electroporation and cells were recovered at 37° C. for 4 h with shaking (180 rpm). Subsequently, 10 µl of chloroform was added to assist host lysis and phage release. Following centrifugation at 12,000×g for 1 min, dilutions of the supernatant were mixed with 200 µL of an overnight culture of *E. coli* Ec20 and 5 mL of molten LC soft agar, layered onto pre-warmed LB plates, and incubated for 16 h at 37° C.

Effector Susceptibility Assessment 400 mL of a log-phase culture of the target bacterial strain was mixed with 10 mL of molten LC soft agar, poured onto a square plate (12×12 cm) containing the appropriate growth agar, and dried for 15 min. 10 mL of each sterile-filtered crude phage lysate was spotted on the bacterial lawn, dried, and incubated overnight to visualize the zones of growth inhibition.

Turbidity Reduction Assays

Log-phase cultures were diluted in BHI-fc (*E. faecalis*) or SHU (*E. coli* and *K. pneumoniae*) to an $OD_{600\ nm}$ of 0.05-0.1, distributed into clear, flat-bottom 96-well plates (Bioswisstech) and infected with phages to obtain a final concentration of $5 \times 10^7$ plaque-forming units (PFU)/mL. The plates were sealed with a microplate sealing film (Axygen™) and $OD_{600\ nm}$ was quantified every 5 min at 30° C. using a spectrophotometer (SPECTROstar Omega or SPECTROstar Nano, BMG Labtech). Uninfected bacterial dilutions were used as growth controls, and growth medium without bacteria was used as a background/sterility control. All cross-genus HEPT experiments used a ratio of 10:1 producer to recipient cells. Experiments were performed as technical triplicates and reported as mean±standard deviation (SD). When indicated, triplicate reactions were combined, serially diluted, and plated on agar plates at 10 or 18 h post-infection.

Time Kill Assays

For cross-genus HEPT TKAs, 1 mL of co-culture was infected with $10^9$ or $5 \times 10^7$ PFU/mL of HEPTs derived from EfS7 and CM001 scaffolds, respectively. The ratio of producer cell to recipient cell was always 10:1 with starting concentrations (CFU/mL) provided in FIG. 6. Differential and selective plating was used to enumerate the different bacterial species. *E. coli* and *K. pneumoniae* were counted on chromogenic coliform agar (CCA, Biolife italiana) and *E. faecalis* was counted on KFS agar (Biolife italiana) after incubation at 37 and 42° C. for 16 or 48 h, respectively. Experiments were performed as biological triplicates and reported as mean±SD.

Repeated Phage Exposure and Resistance Development

*E. coli* strains Ec20 and Ec41 and *K. pneumoniae* strains Kp18, Kp28, and Kp37 were diluted to an $OD_{600\ nm}$ of 0.1 and infected with $10^8$ PFU/mL of phages E2 or K1 (round I) in SHU. After 18 h of infection, the phage-exposed samples were combined (n=3) and diluted to an $OD_{600\ nm}$ of 0.1 in fresh SHU and incubated with additional WT phage or media alone for another 18 h (round II). Individual surviving clones were isolated after 36 h by re-streaking on LB agar and tested in vitro for phage susceptibility using spot-on-the-lawn assays.

Reporter-Phage Based Urinalysis and Ex Vivo Activity Assessment

Reporter phage urinalysis was performed as described previously (1). In brief, 1 mL of patient urine sample was directly mixed with 4 mL of LB. Samples were enriched for 1 h at 37° C. with shaking (180 rpm). 50 µL of reporter phage was added to individual 450 µL aliquots of enriched urine ($10^6$ PFU/mL final concentration) and incubated at 37° C. with shaking. LB media spiked with reporter phages alone served as background controls. Bioluminescence measurements were taken at 3 h post infection. Based on manufacturer's instructions, a buffer-reconstituted NLuc substrate (Nano-Glo Luciferase Assay System, Promega) was mixed at a 1:1 ratio with a sample of the infection mixture (40 µL total) in Nunc™ F96 MicroWell™ plates (Thermo Fisher). Bioluminescence was quantified 5 min after substrate addition using a GloMax® Navigator Luminometer (Promega) with 5 s integration and 2 s delay. Relative light units (RLUs) were background corrected by division of the RLU from phage-only controls. Samples producing $>10^3$ RLU fold change (FC) were considered positive. To confirm reporter phage results and to isolate strains, patient urine was plated on differential agar (UriSelect4, BioRad). *E. coli* isolates were tested for phage-sensitivity by determining the efficiency of plating using the soft-agar-overlay method. For ex vivo TKA experiments, 250 mL of patient urine was infected with 250 mL of a $10^9$ PFU/mL stock of E2 or E2::colE7 in PBS solution, incubated for 24 hours at 37° C., and plated on LB at the indicated time points. T=0 was plated prior to phage addition as an input control. To replicate TKA conditions, in vitro turbidity reduction assays were performed by adding 100 ml of a $10^9$ PFU/mL stock solution of E2 or E2::colE7 to 100 ml of bacterial culture in SHU at a lower starting $OD_{600\ nm}$ of 0.005 to reproduce bacterial loads in patient urine.

Additional data on self-targeting HEPTs phi41S::co/M, phi41S::colE7, CM001::colE7, E2::col5, and phi41S::col5 is depicted in FIG. 14. Additional data on cross-targeting HEPTs K1::col5, K1::colE6, K1::co/K, EfS7::co/M, and EfS7::kvarM is depicted in FIG. 15.

REFERENCES

1. Du, J., Meile, S., Staubli, S., Koliwer-Brandl, H., Piffaretti, P., Leitner, L., Matter, C. I., Baggenstos, J., Milek, S., Gübeli, C. et al. (2022) Engineered reporter phages for rapid detection of *Escherichia coli* and *Klebsiella* spp. in urine. *Cell Rep Med*, submitted.

2. Lima, W. C., Pillonel, T., Bertelli, C., Ifrid, E., Greub, G. and Cosson, P. (2018) Genome sequencing and functional characterization of the non-pathogenic *Klebsiella pneumoniae* KpGe bacteria. *Microbes Infect,* 20, 293-301.

3. Meile, S., Du, J., Grossman, S., Koliwer-Brandl, H., Piffaretti, P., Leitner, L., Baggenstos, J., Matter, C. I., Milek, S., Gübeli, C. et al. (2022) Engineered reporter phages for rapid detection of *Enterococcus faecalis* in urine. *Cell Rep Med,* submitted.

4. Sarigul, N., Korkmaz, F. and Kurultak, I. (2019) A New Artificial Urine Protocol to Better Imitate Human Urine. *Sci Rep,* 9, 20159.

5. Aziz, R. K., Bartels, D., Best, A. A., DeJongh, M., Disz, T., Edwards, R. A., Formsma, K., Gerdes, S., Glass, E. M., Kubal, M. et al. (2008) The RAST Server: rapid annotations using subsystems technology. *BMC Genomics,* 9, 75.

6. Chan, P. P. and Lowe, T. M. (2019) tRNAscan-SE: Searching for tRNA Genes in Genomic Sequences. *Methods Mol Biol,* 1962, 1-14.

7. Kilcher, S., Studer, P., Muessner, C., Klumpp, J. and Loessner, M. J. (2018) Cross-genus rebooting of custom-made, synthetic bacteriophage genomes in L-form bacteria. *Proc Natl Acad Sci USA,* 115, 567-572.

8. Proenca, D., Leandro, C., Garcia, M., Pimentel, M. and Sao-Jose, C. (2015) EC300: a phage-based, bacteriolysin-like protein with enhanced antibacterial activity against *Enterococcus faecalis. Appl Microbiol Biotechnol,* 99, 5137-5149

SEQUENCE LISTING

The patent contains a lengthy sequence listing. A copy of the sequence listing is available in electronic form from the USPTO web site (https://seqdata.uspto.gov/docdetail?docId=US12673078B2). An electronic copy of the sequence listing will also be available from the USPTO upon request and payment of the fee set forth in 37 CFR 1.19(b)(3).

The invention claimed is:

1. A modified bacteriophage capable of infecting a host bacterium, wherein the bacteriophage genome comprises a gene that is foreign to the bacteriophage, wherein said gene encodes a bacteriocin selected from the group consisting of Colicin M as set forth in SEQ ID NO: 18, Colicin E7 as set forth in SEQ ID NO: 20, Colicin K as set forth in SEQ ID NO: 19, Colicin 5 as set forth in SEQ ID NO: 17, Colicin E6 as set forth in SEQ ID NO: 16 and Klebicin M as set forth in SEQ ID NO: 21, while maintaining its wild-type bacteriocin functionality.

2. The modified bacteriophage according to claim 1, wherein the host bacterium is selected from the group consisting of: *Acetinobacter, Chronobacter, Bortadella, Burkholderia, Campylobacter, Staphylococcus, Pneumococcus, Enterococcus, Klebsiella, Escherichia, Pseudomonas, Salmonella, Shigella, Vibrio, Neisseria, Brucella, Haemophilus, Mycobacterium, Listeria, Legionella, Yersinia, Chlamydia, Clostridium, Helicobacter, Corynebacterium, Lactobacillus, Fusobacterium,* and *Streptococcus.*

3. The modified bacteriophage according to claim 1, wherein the host bacterium is an *Escherichia coli (E. coli)* species and wherein the bacteriocin targets said *E. coli* species, or wherein the host bacterium is an *E. coli* species and wherein the bacteriocin does not target said *E. coli* species.

4. The modified bacteriophage according to claim 1, wherein the host bacterium is an *Enterococcus* species, and wherein the bacteriocin targets said *Enterococcus* species, or wherein the host bacterium is an *Enterococcus* species, and wherein the bacteriocin does not target said *Enterococcus* species.

5. The modified bacteriophage according to claim 1, wherein the host bacterium is a *Klebsiella* species, and wherein the bacteriocin targets said *Klebsiella* species or wherein the host bacterium is a *Klebsiella* species, and wherein the bacteriocin does not target said *Klebsiella* species.

6. The modified bacteriophage according to claim 1, wherein the bacteriophage is derived from wild-type bacteriophage *Klebsiella* phage K1, *E. coli* phage CM001, *E. coli* phage E2, *Enterococcus* phage Efs3, *Enterococcus* phage Efs7 or from *E. coli* phage phi41S.

7. A composition comprising a carrier and the modified bacteriophage as defined in claim 1.

8. The composition according to claim 7, wherein the composition is a pharmaceutical composition.

9. The modified bacteriophage according to claim 1, wherein the bacteriocin targets species of the host bacterium, or wherein the bacteriocin does not target species of the host bacterium.

10. The modified bacteriophage according to claim 4, wherein the *Enterococcus* species is *Enterococcus faecalis*.

11. The modified bacteriophage according to claim 5, wherein the *Klebsiella* species is *Klebsiella pneumoniae*.

12. The pharmaceutical composition according to claim 8, wherein the pharmaceutical composition is formulated for topical, intravenous, intramuscular, intrathecal, oral, intraperitoneal, vaginal, rectal, lumbar, or meningeal administration.

13. A method of treatment of a bacterial infection in a subject in need thereof comprising administration of the modified bacteriophage according to claim 1 to the subject.

\* \* \* \* \*